US008653134B2

(12) United States Patent
Vidal et al.

(10) Patent No.: US 8,653,134 B2
(45) Date of Patent: Feb. 18, 2014

(54) HYDROXYPHENOL DERIVATIVES, PROCESSES FOR THE PREPARATION THEREOF, PHARMACEUTICAL COMPOSITIONS THEM, AND THERAPEUTIC USES THEREOF

(75) Inventors: Catherine Vidal, Lyons (FR); Nathalie Adje, Genas (FR); Stéphane Yvon, Ste Foy les Lyon (FR); Jean Jacques Zeiller, Lyons (FR)

(73) Assignee: Merck Patent GmbH, Darmstadt (DE)

( * ) Notice: Subject to any disclaimer, the term of this patent is extended or adjusted under 35 U.S.C. 154(b) by 836 days.

(21) Appl. No.: 11/813,933

(22) PCT Filed: Dec. 22, 2005

(86) PCT No.: PCT/EP2005/013858
§ 371 (c)(1),
(2), (4) Date: Jul. 13, 2007

(87) PCT Pub. No.: WO2006/074798
PCT Pub. Date: Jul. 20, 2006

(65) Prior Publication Data
US 2008/0161308 A1 Jul. 3, 2008

(30) Foreign Application Priority Data
Jan. 14, 2005 (FR) ..................................... 05 00420

(51) Int. Cl.
*A61K 31/085* (2006.01)
*A61K 31/09* (2006.01)
*C07C 233/01* (2006.01)
*C07C 321/14* (2006.01)

(52) U.S. Cl.
USPC ........... 514/529; 514/557; 514/618; 514/621; 560/151; 564/162; 564/169

(58) Field of Classification Search
USPC ........... 560/151; 564/162, 169; 514/529, 557, 514/618, 621
See application file for complete search history.

(56) References Cited

PUBLICATIONS

RN 874487-57-7, retrieved from CAPLUS; retrieved on Mar. 12, 2009.*
Vippagunta, et al. Advanced Drug Delivery Reviews 48 (2001) 3-26.*
Kumar, et al. Document No. 140:357303, retrieved from CAPLUS, 2003.*
He, et al. Document No. 140:339120, retrieved from CAPLUS, 2002.*
Wu, et al. Document No. 129:122870, retrieved from CAPLUS, 1998.*
Akerblom, et al. Document No. 129:202742, retrieved from CAPLUS, 1998.*
Witzel, et al. Document No. 118:233660, retrieved from CAPLUS, 1993.*
D'Antone, et al. Document No. 118:207450, retrieved from CAPLUS, 1993.*
Hayashi, et al. Document No. 100:103037, retrieved from CAPLUS, 1984.*
Wilson, et al. Document No. 100:88338, retrieved from CAPLUS, 1984.*
Samuilov, et al. Document No. 99:157547, retrieved from CAPLUS, 1983.*
Mydilova, et al. Document No. 76:95614, retrieved from CAPLUS, 1971.*
Besace, et al. Document No. 75:88236, retrieved from CAPLUS, 1971.*
McLoughlin, et al. Document No. 75:76811, retrieved from CAPLUS, 1971.*
Mameli, et al. Document No. 14:16427, retrieved from CAPLUS, 1920.*
Nelson. Document No. 14:2876, retrieved from CAPLUS, 1920.*
Patel, et al. Document No. 150:351658, retrieved from CAPLUS, 20061214.*
Balachandran, et al. Document No. 148:121695, retrieved from CAPLUS, 20050407.*
Database Beilstein Beilstein Institut Zur Foerderung Der Chemischen Wissenschaften, Frankfurt Am Main, DE; XP002348755 Database accession No. BRN2529202 abstract & Smereczynski et al: Bull. Acad. Pol. Sci. Ser. Sci. Chim., vol. 15, 1967, pp. 65-69, & Anal . Stiint. Univ. Lasi, vol. 2, 1956, pp. 257-259.
Database Beilstein Beilstein Institut Zur Foerderung Der Chemischen Wissenschaften, Frankfurt Am Main, DE; XP002348756 Database accession No. BRN7269113 abstract & Smereczynski et al: Bull. Acad. Pol. Sci. Ser. Sci. Chim., vol. 15, 1967, pp. 65-69.
Database Beilstein Beilstein Institut Zur Foerderung Der Chemischen Wissenschaften, Frankfurt Am Main, DE; XP002348757 Database accession No. BRN3344561 abstract & Arventiev: Anal. Stiint. Univ. Lasi, vol. 2, 1956, pp. 257-259.

(Continued)

*Primary Examiner* — Shawquia Young
(74) *Attorney, Agent, or Firm* — Millen, White, Zelano & Branigan, P.C.

(57) ABSTRACT

Compounds of the formula (I): in which A, $R^1$, $R^2$, X, Y and Z are defined in the description, the processes for the preparation of these compounds, the uses thereof for the treatment of dyslipidaemia, atherosclerosis and diabetes, and the pharmaceutical compositions comprising them.

(1)

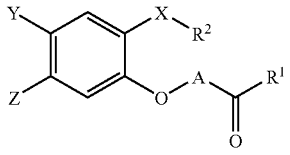

13 Claims, No Drawings

(56) References Cited

PUBLICATIONS

Database Beilstein Beilstein Institut Zur Foerderung Der Chemischen Wissenschaften, Frankfurt Am Main, DE; XP002348758 Database accession No. BRN3296620 abstract & Freudenberg et al: Justus Liebigs Ann. Chem., vol. 584, 1953, pp. 40-48.

Database Beilstein Beilstein Institut Zur Foerderung Der Chemischen Wissenschaften, Frankfurt Am Main, DE; XP002348759 Database accession No. BRN3296601 abstract & Freudenberg et al: Justus Liebigs Ann. Chem., vol. 584, 1953, pp. 40-48.

Database Beilstein Beilstein Institut Zur Foerderung Der Chemischen Wissenschaften, Frankfurt Am Main, DE; XP 002348760 Database accession No. BRN3269681 abstract and DE 157 355 A 1902.

Database Beilstein Beilstein Institut Zur Foerderung Der Chemischen Wissenschaften, Frankfurt Am Main, DE; XP 002348761 Database accession No. BRN2585732 abstract & Naito et al: Chem. Pharm. Bull., vol. 17, 1969, pp. 1794-1798.

Database Beilstein Beilstein Institut Zur Foerderung Der Chemischen Wissenschaften, Frankfurt Am Main, DE; XP 002348762 Database accession No. BRN2562662 abstract & Rottendorf: Aust. J. Chem, vol. 16, 1963, pp. 647-657.

Database Beilstein Beilstein Institut Zur Foerderung Der Chemischen Wissenschaften, Frankfurt Am Main, DE; XP 002348763 Database accession No. BRN1874501 abstract & Cohn: J. Prakt. Chem., vol. 63, 1901, p. 188.

Hulin et al: "The Glitazone Family of Antidiabetic Agents" Current Pharmaceutical Design, vol. 2, 1996, pp. 85-102, XP000940783.

Berger et al: "Novel Peroxisome Proliferator—activated Receptor" The Journal of Biological Chemistry, vol. 274, 1999, pp. 6718-6725, XP002158742.

* cited by examiner

HYDROXYPHENOL DERIVATIVES, PROCESSES FOR THE PREPARATION THEREOF, PHARMACEUTICAL COMPOSITIONS THEM, AND THERAPEUTIC USES THEREOF

The present invention relates to hydroxyphenol derivatives that can be used in the treatment of dyslipidaemia, atherosclerosis and diabetes. The invention also relates to pharmaceutical compositions comprising them and to processes for the preparation of these compounds.

In addition, the invention relates to the use of these compounds for the production of medicaments for the treatment of dyslipidaemia, atherosclerosis and diabetes.

The chronic effect of a calorie imbalance has resulted in an epidemic increase in the incidence of metabolic diseases in modern society. As a result, the World Health Organization has estimated that the global incidence of type 2 diabetes will exceed 300 million in 2030. Although several therapeutic options exist, none of them reverses the progress of this plague.

Although the control of glycated haemoglobin and plasmatic glycaemia in the fasted state are still considered as the primary objectives of antidiabetic treatments, acknowledgement of the fact that the diabetic state encompasses a range of metabolic disorders has broadened scope and expectations of future therapies. In the course of the last decade, hyperglycaemia has been shown to be not the only component of a series of anomalies affecting type-2 diabetic patients. Concurrent diseases, including insulin resistance, obesity, hypertension and dyslipidaemia, which, if they are present together or in part, constitutes what has been described as metabolic syndrome or syndrome X. This array of metabolic disorders forms the bases of a substantial increase in the incidence of cardiovascular disease in these patients.

In the search for novel and improved treatment options for diabetic patients, the family of receptors activated by the peroxisome proliferators ("peroxisome proliferator-activated receptor": PPAR) appears potentially to be an ideal target. This family of ligand-activated transcription factors modulates numerous aspects of lipid and carbohydrate metabolism, thus having the possibility of attacking several facets of the diabetic phenotype. There are three types of PPAR: PPAR alpha, gamma and delta (PPARα, PPARγ and PPARδ, respectively).

PPARα is involved in stimulating the β-oxidation of fatty acids. In rodents, a change transmitted by a PPARα in the expression of genes involved in fatty acid metabolism is the basis of the phenomenon of peroxisome proliferation, a pleiotropic cellular response, mainly limited to the liver and the kidneys, which can lead to hepatocarcinogenesis in rodents. The phenomenon of peroxisome proliferation is not encountered in man. In addition to its role in peroxisome proliferation in rodents, PPARα is also involved in controlling the levels of HDL cholesterol in rodents and humans. This effect is at least partially based on a transcription regulation transmitted by a PPARα of the major HDL apolipoproteins, apo A-I and apo A-II. The hypo-triglyceridaemiant action of fibrates and fatty acids also involves PPARα and can be summarised as follows: (i) increased lipolysis and clearance of the remaining particles, due to changes in the levels of lipoprotein lipase and of apo C-III, (ii) stimulation of fatty acid uptake by the cell and its subsequent conversion into acyl-CoA derivatives by induction of a protein for binding fatty acids and acyl-CoA synthase, (iii) induction of the β-oxidation pathways of fatty acids, (iv) reduction in the synthesis of fatty acids and triglycerides, and finally (v) reduction in the production of VLDL. As a result, both the improved catabolism of the triglyceride-rich particles and the reduced secretion of VLDL particles constitute mechanisms that contribute towards the hypo-lipidaemiant effect of fibrates.

Fibric acid derivatives, such as clofibrate, fenofibrate, benzafibrate, ciprofibrate, beclofibrate and etofibrate, and also gemfibrozil, each of which are PPARα ligands and/or activators, produce a substantial reduction in plasmatic triglycerides and also a certain increase in HDLs. The effects on LDL cholesterol are contradictory and may depend on the compound and/or the dyslipidaemic phenotype. For these reasons, this class of compounds was first used for the treatment of hypertriglyceridaemia (i.e. Fredrickson Type IV and V) and/or mixed hyperlipidaemia.

The activation of a PPARδ was initially reported as not being involved in the modulation of the levels of glucose or of triglycerides (Berger et al., *J. Biol. Chem.*, (1999), Vol. 274, pp. 6718-6725). Later, it was shown that the activation of PPARδ leads to higher levels of HDL cholesterol in dbldb mice (Leibowitz et al., *FEBS Letters*, (2000), 473, 333-336). Furthermore, a PPARδ agonist, during its administration to obese adult insulin-resistant rhesus monkeys, caused a dramatic dose-dependent increase in HDL cholesterol in the serum, while at the same time reducing the levels of low-density LDLs, by depleting the triglycerides and the insulin (Oliver et al., *PNAS*, (2001), 98, 5306-5311). The same publication also showed that the activation of PPARδ increased the AI cassette binding the ATP inverse transporter of cholesterol and induced a flow of cholesterol specific for apolipoprotein A1. Taken together, these observations suggest that the activation of PPARδ is useful for the treatment of and preventing diseases and cardiovascular states comprising atherosclerosis, hypertriglyceridaemia and mixed dyslipidaemia (PCT publication WO 01/00603 (Chao et al.)).

The subtypes of PPARγ receptor are involved in the activation of the programme of adipocyte differentiation and are not involved in the stimulation of peroxisome proliferation in the liver. There are two known isoforms of PPARγ protein: PPARγ1 and PPARγ2, which differ only in the fact that PPARγ2 contains 28 additional amino acids at the amino end. The DNA sequences for the human isotypes are described by Elbrecht et al., *BBRC,* 224, (1996), 431-437. In mice, PPARγ2 is specifically expressed in the fat cells. Tontonoz et al., *Cell,* 79, (1994), 1147-1156, provide proof showing that one physiological role of PPARγ2 is to induce adipocyte differentiation. As with other members of the superfamily of nuclear hormone receptors, PPARγ2 regulates the expression of genes via an interaction with other proteins and binding to hormone response elements, for example in the 5' lateral regions of the response genes. An example of a PPARγ2 response gene is the tissue-specific P2 adipocyte gene. Although peroxisome proliferators, comprising fibrates and fatty acids, activate the transcriptional activity of PPAR receptors, only prostaglandin $J_2$ derivatives have been identified as potential natural ligands of the PPARγ subtype, which also binds antidiabetic thiazolidinedione agents with high affinity.

It is generally thought that glitazones exert their effects by binding to receptors of the family of peroxisome proliferator-activated receptors (PPAR), by controlling certain transcription elements in relation with the biological species listed above. See Hulin et al., *Current Pharm. Design*, (1996), 2, 85-102. In particular, PPARγ has been imputed as a major molecular target for the glitazone class of insulin sensitisers.

Many compounds of glitazone type, which are PPAR agonists, have been approved for use in the treatment of diabetes.

These are troglitazone, rosiglitazone and pioglitazone, which are all primary or exclusive agonists of PPARγ.

This indicates that the search for compounds having varying degrees of PPARα, PPARγ and PPARδ activation might lead to the discovery of medicaments that efficiently reduce triglycerides and/or cholesterol and/or glucose, presenting great potential in the treatment of diseases, such as type 2 diabetes, dyslipidaemia, syndrome X (comprising metabolic syndrome, i.e. reduced glucose tolerance, insulin resistance, hypertriglyceridaemia and/or obesity), cardiovascular diseases (comprising atherosclerosis) and hypercholesterolaemia.

The combinations of the PPAR activities that have been studied the most extensively are the PPAR alpha plus gamma combination (dual agonists) with, especially, tesaglitazar, and also the alpha, gamma plus delta triple combination (PPAR-pan agonists).

Although glitazones are beneficial in the treatment of NIDDM, a number of serious unfavourable side effects associated with the use of these compounds have been found. The most serious of these was toxicity to the liver, which has resulted in a certain number of deaths. The most serious problems arose in the use of troglitazone, which has recently been removed from the market for toxicity reasons.

Besides the potential hepatic toxicity of glitazones, other deleterious effects have been associated with PPAR gamma full agonists, for instance weight gain, anaemia and oedema, which limit their use (rosiglitazone, pioglitazone).

On account of the problems that have been encountered with glitazones, researchers in many laboratories have studied classes of PPAR agonists that are not glitazones and do not contain 1,3-thiazolidinedione species, but which modulate the three known subtypes of PPAR, together or separately, to variable degrees (measured by intrinsic power, maximum breadth of functional response or spectrum of changes in gene expression).

Thus, recent studies (cf. WO 01/30343 and WO 02/08188) have revealed that certain compounds have PPAR agonist or partial agonist properties, which are useful in the treatment of type 2 diabetes with reduced side effects with respect to the heart weight and body weight.

The inventors have now discovered a novel class of compounds that are partial or full agonists of PPARγ, with differing degrees of PPARα and/or PPARδ activity.

More specifically, the invention relates to hydroxyphenol-based compounds of the formula (1) below:

(1)

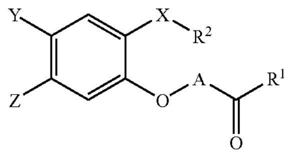

in which:

$R^1$ represents —O—$R'^1$ or —$NR'^1R''^1$, with $R'^1$ and $R''^1$, which may be identical or different, being chosen from a hydrogen atom, an alkyl radical, an alkenyl radical, an alkynyl radical, a cycloalkyl radical, an aryl radical and a heteroaryl radical;

A represents a linear or branched, saturated or unsaturated divalent hydrocarbon-based radical containing from 1 to 10 carbon atoms;

$R^2$ is chosen from:

an alkyl, alkenyl or alkynyl radical;

an optionally substituted cycloalkylalkyl radical;

an optionally substituted arylalkyl radical; and an optionally substituted heterocyclylalkyl radical;

X is chosen from an oxygen atom and a sulfur atom;

Y and Z, which may be identical or different, are chosen, independently of each other, from a hydrogen atom, a halogen atom, an alkyl radical and a radical —O—$R^3$, —C(O)—$R^3$, —C(O)—$NHR^3$ or —C(O)—$NR^3R^4$; or Y and Z together form, with the carbon atoms that bear them, a 5-membered ring comprising a ketone function; and $R^3$ and $R^4$, which may be identical or different, are chosen, independently of each other, from a hydrogen atom and an alkyl radical, or $R^3$ and $R^4$ together form, with the nitrogen atom that bears them, an optionally substituted heterocycle;

the possible optical isomers, oxide forms and solvates thereof, and also the pharmaceutically acceptable addition salts thereof with acids or bases.

The acids that can be used for the formation of salts of compounds of the formula (1) are mineral or organic acids. The resulting salts are, for example, the hydrochlorides, hydrobromides, sulfates, hydrogen sulfates, dihydrogen phosphates, citrates, maleates, fumarates, trifluoro-acetates, 2-naphthalenesulfonates and para-toluenesulfonates.

The bases that can be used for the formation of salts of compounds of the formula (1) are organic or mineral bases. The resulting salts are, for example, the salts formed with metals and especially alkali metals, alkaline-earth metals and transition metals (such as sodium, potassium, calcium, magnesium or aluminium) or with bases, for instance ammonia or secondary or tertiary amines (such as diethylamine, triethylamine, piperidine, piperazine or morpholine) or with basic amino acids, or with osamines (such as meglumine) or with amino alcohols (such as 3-aminobutanol and 2-aminoethanol).

The invention especially encompasses the pharmaceutically acceptable salts, but also salts that allow a suitable separation or crystallisation of the compounds of the formula (1), such as the salts obtained with chiral amines or chiral acids.

Examples of chiral amines that can be used include quinine, brucine, (S)-1-(benzyloxymethyl)propylamine (III), (−)-ephedrine, (4S,5R) -(+)-1,2,3,4-tetramethyl-5-phenyl-1,3-oxazolidine, (R)-1-phenyl-2-p-tolylethy-lamine, (S)-phenylglycinol, (−)—N-methylephedrine, (+)-(2S,3R)-4-dimethyl-amino-3-methyl-1,2-diphenyl-2-butanol, (S)-phenylglycinol and (S)-α-methyl-benzylamine, or a mixture of two or more thereof.

Examples of chiral acids that can be used include (+)-d-di-O-benzoyltartaric acid, (−)-1-di-O-benzoyltartaric acid, (−)-di-O,O'-p-toluoyl-I-tartaric acid, (+)-di-O,O'-p-toluoyl-d-tartaric acid, (R)-(+)-malic acid, (S)-(−)-malic acid, (+)-camphanic acid, (−)-camphanic acid, R-(−)-1,1'-binaphthalene-2,2'-diyl hydrogen phosphate, (S)-(+)-1,1'-binaphthalene-2,2'-diyl hydrogen phosphate, (+)-camphoric acid, (−)-camphoric acid, (S)-(+)-2-phenylpropionic acid, (R)-(−)-2-phenylpropionic acid, d-(−)-mandelic acid, I-(+)-mandelic acid, d-tartaric acid and I-tartaric acid, or a mixture of two or more thereof.

The chiral acid is preferably chosen from (−)-di-O,O'-p-toluoyl-1-tartaric acid, (+)-di-O,O'-p-toluoyl-d-tartaric acid, (R)-(−)-1,1'-binaphthalene-2,2'-diyl hydrogen phosphate, (S)-(+)-1,1'-binaphthalene-2,2'-diyl hydrogen phosphate, d-tartaric acid and L-tartaric acid, or a mixture of two or more thereof.

The invention also encompasses the possible optical isomers, in particular stereoisomers and diastereoisomers, where appropriate, of the compounds of the formula (1), and also mixtures of the optical isomers in any proportions, including racemic mixtures.

Depending on the nature of the substituents, the compounds of the formula (1) may also be in various tautomeric forms, which are also included in the present invention, alone or as mixtures of two or more thereof, in all proportions.

The compounds of the formula (1) above also include the prodrugs of these compounds.

The term "prodrugs" means compounds which, once administered to the patient, are chemically and/or biologically converted by the living body, into compounds of the formula (1).

In the compounds of the formula (1) defined above, the term "alkyl radical" means a linear or branched hydrocarbon-based chain containing from 1 to 10 carbon atoms and better still from 1 to 6 carbon atoms, for example from 1 to 4 carbon atoms.

Examples of alkyl radicals are methyl, ethyl, propyl, isopropyl, butyl, isobutyl, tert-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl and 7,7-dimethyloctyl.

The alkyl radicals present as substituents of the compounds of the formula (1) according to the present invention may be optionally substituted by one or more chemical species chosen from:

- halogen atom;
- —O-alkyl radical;
- aryl radical;
- cycloalkyl radical; and
- heterocyclic radical.

The term "alkenyl radical" means a linear or branched hydrocarbon-based chain containing from 2 to 10 carbon atoms, preferably from 2 to 8 carbon atoms and advantageously from 2 to 6 carbon atoms, containing one, two or more unsaturations in the form of a double bond, the said chain being optionally substituted by one or more substituents, which may be identical or different, chosen from halogen atoms and trifluoromethyl, trifluoromethoxy, hydroxyl, alkoxy, alkoxycarbonyl, carboxyl and oxo radicals.

Examples of alkenyl radicals that may be mentioned include the ethylenyl radical, the propenyl radical, the isopropenyl radical, the but-2-enyl radical, pentenyl radicals and hexenyl radicals.

The term "alkynyl radical" means a linear or branched hydrocarbon-based chain containing from 2 to 10 carbon atoms, preferably from 2 to 8 carbon atoms and advantageously from 2 to 6 carbon atoms, containing one, two or more unsaturations in the form of a triple bond, the said chain being optionally substituted by one or more substituents, which may be identical or different, chosen from halogen atoms and trifluoromethyl, trifluoromethoxy, hydroxyl, alkoxy, alkoxycarbonyl, carboxyl and oxo radicals.

Examples of alkynyl radicals that may be mentioned include the ethynyl radical, the propynyl radical, the but-2-ynyl radical, pentynyl radicals and hexynyl radicals.

The term "linear or branched, saturated or unsaturated divalent hydrocarbon-based radical containing from 1 to 10 carbon atoms and advantageously from 1 to 6 carbon atoms" means a divalent radical of linear or branched aliphatic hydrocarbon-based type derived from the alkyl groups defined above by abstraction of a hydrogen atom. Preferred examples of alkylenediyl chains are the chains $—(CH_2)_k—$ in which k represents an integer chosen from 1, 2, 3, 4, 5 and 6, and the chains $>CH(CH_3)$, $>C(CH_3)_2$, $—CH_2—CH(CH_3)—CH_2—$ and $—CH_2—C(CH_3)_2—CH_2—$.

This definition also includes divalent radical is comprising a linear or branched hydrocarbon-based chain, as defined above, linked to an ortho-, meta- or para-phenylene ring. Preferred examples of these divalent radicals bearing a phenylene are the radicals $—CH_2$-o-phenylene-, $—CH_2$-m-phenylene-, and $—CH_2$-p-phenylene-, and more preferably the radicals $CH_2$-m-phenylene-, and $—CH_2$-p-phenylene-.

The term "cycloalkylalkyl radical" denotes a radical in which the alkyl portion is as defined above and the cycloalkyl portion represents a monocyclic, bicyclic or tricyclic radical optionally comprising one or more unsaturations in the form of double bonds.

Preferably, the cycloalkyl radical consists of one or more monocycles, each of which is 5- to 8-membered.

Examples of cycloalkyl radicals that may appear in the compounds of the present invention are especially cyclopentyl, cyclopentenyl, cyclohexyl, cyclohexenyl, cyclohexadienyl, cycloheptyl, cycloheptenyl and cycloheptadienyl radicals, to name but a few examples of monocycles.

The polycyclic cycloalkyl radicals are, for example, tetrahydronaphthyl, perhydronaphthyl, indanyl, bicyclooctyl, bicyclononyl and bicyclodecyl radicals.

The term "arylalkyl" denotes a radical in which the alkyl portion is as defined above and the aryl portion denotes a monocyclic or polycyclic carbocyclic aromatic radical containing from 6 to 18 carbon atoms and preferably from 6 to 10 carbon atoms. Aryl radicals that may be mentioned include phenyl, naphthyl, anthryl and phenanthryl radicals.

Unless otherwise indicated, the heterocyclic portion of the heterocyclylalkyl radicals corresponds to a saturated, unsaturated or aromatic, 5- to 8-membered heterocyclic radical containing one or more hetero atoms generally chosen from O, S and N, optionally in oxidised form (in the case of S and N), and optionally one or more unsaturations in the form of double bonds. If they are totally saturated, the heterocyclic radicals are said to be aromatic or heteroaryl radicals.

Preferably, at least one of the monocycles constituting the heterocycle contains from 1 to 4 endocyclic hetero atoms and better still from 1 to 3 hetero atoms.

Preferably, the heterocycle consists of one or more monocycles, each of which is 5- to 8-membered.

Examples of 5- to 8-membered monocyclic aromatic heterocyclic radicals are the heteroaryl radicals derived, by abstraction of a hydrogen atom, from aromatic heterocycles, such as pyridine, furan, thiophene, pyrrole, imidazole, thiazole, isoxazole, isothiazole, furazane, pyridazine, pyrimidine, pyrazine, thiazines, oxazole, pyrazole, oxadiazole, triazole and thiadiazole.

Preferred aromatic heterocyclic radicals that may be mentioned include pyridyl, pyrimidinyl, triazolyl, thiadiazolyl, oxazolyl, thiazolyl and thienyl radicals.

Examples of bicyclic heteroaryls in which each monocycle is 5- to 8-membered are chosen from indolizine, indole, isoindole, benzofuran, benzothiophene, indazole, benzimidazole, benzothiazole, benzofurazane, benzothiofurazane, purine, quinoline, isoquinoline, cinnoline, phthalazine, quinazoline, quinoxaline, naphthyridines, pyrazolotriazines (such as pyrazolo-1,3,4-triazine), pyrazolopyrimidine and pteridine.

Preferred heteroaryl radicals that may be mentioned include the quinolyl, pyridyl, benzothiazolyl and triazolyl radicals.

The tricyclic heteroaryls in which each monocycle is 5- to 8-membered are chosen, for example, from acridine, phenazine and carbazole.

Saturated or unsaturated, 5- to 8-membered monocyclic heterocycles are the saturated or, respectively, unsaturated derivatives of the aromatic heterocycles mentioned above.

More particularly, mention may be made of morpholine, piperidine, thiazolidine, oxazolidine, tetrahydrothienyl, tetrahydrofuryl, pyrrolidine, isoxazolidine, imidazolidine and pyrazolidine.

If the radicals defined above are qualified by "optionally substituted", they may contain one or more substituents chosen from halogen atom, alkyl radical, alkoxy radical, trifluoromethyl, trifluoromethoxy, styryl, monocyclic, bicyclic or tricyclic aromatic heterocyclic radical containing one or more hetero atoms chosen from O, N and S; and optionally substituted by one or more radicals T as defined below; group Het-CO— in which Het represents an aromatic heterocyclic radical as defined above, optionally substituted by one or more radicals T; a $C_1$-$C_6$ alkylene chain; a $C_1$-$C_6$-alkylenedioxy chain; nitro; cyano; $(C_1$-$C_{10})$alkyl; $(C_1$-$C_{10})$alkylcarbonyl; $(C_1$-$C_{10})$alkoxy-carbonyl-A- in which A represents $(C_1$-$C_6)$alkylene, $(C_2$-$C_6)$alkenylene or a bond; $(C_3$-$C_{10})$cycloalkyl; trifluoromethoxy; di$(C_1$-$C_{10})$alkylamino; $(C_1$-$C_{10})$-alkoxy$(C_1$-$C_{10})$alkyl; $(C_1$-$C_{10})$alkoxy; $(C_6$-$C_{18})$aryl optionally substituted by one or more radicals T; $(C_6$-$C_{18})$aryl$(C_1$-$C_{10})$alkoxy$(CO)_n$— in which n is 0 or 1 and aryl is optionally substituted by one or more radicals T; $(C_6$-$C_{18})$aryloxy-$(CO)_n$— in which n is 0 or 1 and aryl is optionally substituted by one or more radicals T; $(C_6$-$C_{18})$arylthio in which aryl is optionally substituted by one or more radicals T; $(C_6$-$C_{18})$aryloxy$(C_1$-$C_{10})$alkyl$(CO)_n$— in which n is 0 or 1 and aryl is optionally substituted by one or more radicals T; a saturated or unsaturated, 5- to 8-membered monocyclic heterocyclic or heterocyclylalkyl radical containing one or more hetero atoms chosen from O, N and S, optionally substituted by one or more radicals T; $(C_6$-$C_{18})$arylcarbonyl optionally substituted by one or more radicals T; $(C_6$-$C_{18})$arylcarbonyl-B—$(CO)_n$— in which n is 0 or 1; B represents $(C_1$-$C_6)$alkylene or $(C_2$-$C_6)$alkenylene and aryl is optionally substituted by one or more radicals T; $(C_6$-$C_{18})$aryl-C—$(CO)_n$— in which n is 0 or 1, C represents $(C_1$-$C_6)$alkylene or $(C_2$-$C_6)$alkenylene and aryl is optionally substituted by one or more radicals T; $(C_6$-$C_{18})$aryl fused with a saturated or unsaturated heterocycle as defined above, optionally substituted by one or more radicals T; and $(C_2$-$C_{10})$alkynyl.

T is chosen from a halogen atom; $(C_6$-$C_{18})$aryl; $(C_1$-$C_6)$alkyl; $(C_1$-$C_6)$alkoxy; $(C_1$-$C_6)$alkoxy$(C_6$-$C_{18})$aryl; nitro; carboxyl; $(C_1$-$C_6)$alkoxycarboxyl; and T may represent oxo if it substitutes a saturated or unsaturated heterocycle; or alternatively T represents $(C_1$-$C_6)$alkoxycarbonyl$(C_1$-$C_6)$alkyl; or $(C_1$-$C_6)$alkylcarbonyl$((C_1$-$C_6)$alkyl$)_n$- in which n is 0 or 1.

The term "halogen atom" means a chlorine, bromine, iodine or fluorine atom, preferably fluorine or chlorine.

Among the compounds of the formula (1), the ones that are preferred are those for which $R^1$ represents —O—R'$^1$ and most particularly those for which $R^1$ represents —O—R'$^1$, R'$^1$ being a hydrogen atom or an alkyl radical.

A first preferred group of compounds of the invention consists of compounds having one or more of the following characteristics, taken separately or as a combination of one, several or all of them:

$R^1$ represents —O—R'$^1$, with R'$^1$ being chosen from a hydrogen atom and an alkyl radical;

A represents a linear or branched, saturated or unsaturated divalent hydrocarbon-based radical containing from 1 to 6 carbon atoms, or a linear or branched hydrocarbon-based chain containing from 1 to 6 carbon atoms, linked to an ortho-, meta- or para-phenylene ring;

$R^2$ is chosen from an alkyl radical, a cycloalkylalkyl radical, an arylalkyl radical and a heterocyclylalkyl radical, which is optionally substituted;

X is chosen from an oxygen atom and a sulfur atom;

Y and Z, which may be identical or different, are chosen, independently of each other, from a hydrogen atom, a halogen atom and a radical —O—$R^3$, —C(O)—$R^3$, —C(O)—NH$R^3$ or —C(O)—N$R^3R^4$; or Y and Z together form, with the carbon atoms that bear them, a 5-membered ring comprising a ketone function; and $R^3$ and $R^4$, which may be identical or different, are chosen, independently of each other, from a hydrogen atom and an alkyl radical containing from 1 to 4 carbon atoms, or $R^3$ and $R^4$ together form, with the nitrogen atom that bears them, a 6-membered heterocycle optionally comprising another hetero atom (other than the nitrogen atom that bears them), chosen from N, O and S;

the possible optical isomers, oxide forms and solvates thereof, and also the pharmaceutically acceptable addition salts thereof with acids or bases.

Another even more preferred group of compounds of the invention consists of compounds having one or more of the following characteristics, taken separately or as a combination of one, several or all of them:

$R^1$ represents —O—R'$^1$, with R'$^1$ being chosen from a hydrogen atom, a methyl radical and an ethyl radical;

A represents a linear or branched, saturated or unsaturated divalent hydrocarbon-based radical containing from 1 to 3 carbon atoms, or a linear or branched hydrocarbon-based chain containing from 1 to 3 carbon atoms, linked to an ortho-, meta- or para-phenylene ring;

$R^2$ is chosen from an alkyl radical containing from 1 to 6 carbon atoms, a cycloalkylalkyl radical, an arylalkyl radical and a heterocyclylalkyl radical, which is optionally substituted;

X is chosen from an oxygen atom and a sulfur atom;

Y and Z, which may be identical or different, are chosen, independently of each other, from a hydrogen atom, a halogen atom and a radical —O—$R^3$, —C(O)—$R^3$, —C(O)—NH$R^3$ or —C(O)—N$R^3R^4$; or Y and Z together form, with the carbon atoms that bear them, a 5-membered ring comprising a ketone function; and $R^3$ and $R^4$, which may be identical or different, are chosen, independently of each other, from a hydrogen atom and an alkyl radical containing from 1 to 3 carbon atoms, or $R^3$ and $R^4$ together form, with the nitrogen atom that bears them, a 6-membered heterocycle optionally comprising another hetero atom (other than the nitrogen atom that bears them), chosen from N, O and S;

the possible optical isomers, oxide forms and solvates thereof, and also the pharmaceutically acceptable addition salts thereof with acids or bases.

Another preferred group of compounds of the invention consists of compounds having one or more of the following characteristics, taken separately or as a combination of one, several or all of them:

$R^1$ represents a hydroxyl radical;

A represents —$CH_2$—, —$(CH_2)_3$—, —$C(CH_3)_2$—, —$CH_2$-m-phenylene or —$CH_2$-p-phenylene;

$R^2$ is chosen from an alkyl radical containing from 1 to 6 carbon atoms, a cycloalkylalkyl radical, an arylalkyl radical and a heterocyclylalkyl radical, which is optionally substituted;

X is chosen from an oxygen atom and a sulfur atom;

Y and Z, which may be identical or different, are chosen, independently of each other, from a hydrogen atom, a halogen atom and a radical —O—$R^3$, —C(O)—$R^3$, —C(O)—$NHR^3$ or —C(O)—$NR^3R^4$; or Y and Z together form, with the carbon atoms that bear them, a 5-membered ring comprising a ketone function; and $R^3$ and $R^4$, which may be identical or different, are chosen, independently of each other, from a hydrogen atom, a methyl radical and an ethyl radical, or $R^3$ and $R^4$ together form, with the nitrogen atom that bears them, a saturated 6-membered heterocycle optionally comprising another hetero atom (other than the nitrogen atom that bears them), chosen from N and O;

the possible optical isomers, oxide forms and solvates thereof, and also the pharmaceutically acceptable addition salts thereof with acids or bases.

The possible substituents on the radicals defined above for the compounds of the formula (1) are preferably chosen from halogen atoms, preferably fluorine and/or chlorine, and methyl, ethyl, methoxy, phenyl, trifluoromethyl and trifluoromethoxy radicals.

The heterocyclic radicals are preferentially chosen from thienyl, benzothiophenyl, pyridyl, morpholino, piperidino and oxazolyl radicals.

The compounds of the formula (1) that are more particularly preferred are chosen from:

4-[6-(2-cyclohexylethoxy)-3-oxoindan-5-yloxy]butanoic acid;
4-(6-hexyloxy-3-oxoindan-5-yloxy)butanoic acid;
4-(3-oxo-6-pentyloxyindan-5-yloxy)butanoic acid;
3-(3-oxo-6-propylsulfanylindan-5-yloxymethyl)benzoic acid;
4-(6-cyclohexylmethoxy-3-oxoindan-5-yloxy)butanoic acid;
3-(3-oxo-6-pentyloxyindan-5-yloxymethyl)benzoic acid;
4-(3-oxo-6-pentyloxyindan-5-yloxymethyl)benzoic acid;
3-[6-(3-methylbenzylsulfanyl)-3-oxoindan-5-yloxymethyl]benzoic acid;
4-[6-(5-methyl-2-phenyloxazol-4-ylmethoxy)-3-oxoindan-5-yloxy]-butanoic acid;
3-[6-(4-fluorobenzylsulfanyl)-3-oxoindan-5-yloxymethyl]benzoic acid;
3-[6-(3-fluorobenzylsulfanyl)-3-oxoindan-5-yloxymethyl]benzoic acid;
3-[6-(4-methylbenzylsulfanyl)-3-oxoindan-5-yloxymethyl]benzoic acid;
3-{6-[2-(4-methoxyphenyl)ethylsulfanyl]-3-oxoindan-5-yloxymethyl}benzoic acid;
3-(6-cyclohexylmethoxy-3-oxoindan-5-yloxymethyl) benzoic acid;
2-methyl-2-(3-oxo-6-pentyloxyindan-5-yloxy)propanoic acid;
2-methyl-2-(3-oxo-6-phenethyloxyindan-5-yloxy)propanoic acid;
3-(3-oxo-6-phenethyloxyindan-5-yloxymethyl)benzoic acid;
3-{2-[2-(5-methyl-2-phenyloxazol-4-yl)ethoxy]phenoxymethyl}benzoic acid;
3-[2-(2-cyclohexylethoxy)phenoxymethyl]benzoic acid;
3-(5-methoxy-2-pentyloxyphenoxymethyl)benzoic acid; and
3-(5-diethylcarbamoyl-2-pentyloxyphenoxymethyl)benzoic acid;

and from the possible optical isomers, oxide forms and solvates, and also the pharmaceutically acceptable addition salts with acids or bases, of these compounds.

The invention also relates to pharmaceutical compositions comprising a pharmaceutically effective amount of at least one compound of the formula (1) as defined above in combination with one or more pharmaceutically acceptable vehicles.

These compositions can be administered orally in the form of tablets, gel capsules or granules with immediate release or controlled release, intravenously in the form of an injectable solution, transdermally in the form of an adhesive transdermal device, or locally in the form of a solution, cream or gel.

A solid composition for oral administration is prepared by adding to the active principle a filler and, where appropriate, a binder, a disintegrant, a lubricant, a dye or a flavour enhancer, and by forming the mixture into a tablet, a coated tablet, a granule, a powder or a capsule.

Examples of fillers include lactose, corn starch, sucrose, glucose, sorbitol, crystalline cellulose and silicon dioxide, and examples of binders include poly(vinyl alcohol), poly (vinyl ether), ethylcellulose, methylcellulose, acacia, gum tragacanth, gelatine, shellac, hydroxypropylcellulose, hydroxypropylmethylcellulose, calcium citrate, dextrin and pectin. Examples of lubricants include magnesium stearate, talc, polyethylene glycol, silica and hardened plant oils. The dye can be any dye permitted for use in medicaments. Examples of flavour enhancers include cocoa powder, mint in herb form, aromatic powder, mint in oil form, borneol and cinnamon powder. Needless to say, the tablet or granule may be appropriately coated with sugar, gelatine or the like.

An injectable form comprising the compound of the present invention as active principle is prepared, where appropriate, by mixing the said compound with a pH regulator, a buffer, a suspending agent, a solubilising agent, a stabilizer, a tonicity agent and/or a preserving agent, and by converting the mixture into a form for intravenous, subcutaneous or intramuscular injection according to a standard process. Where appropriate, the injectable form obtained can be freeze-dried via a standard process.

Examples of suspending agents include methylcellulose, polysorbate 80, hydroxyethylcellulose, acacia, powdered gum tragacanth, sodium carboxymethyl cellulose and polyethoxylated sorbitan monolaurate.

Examples of solubilising agents include castor oil solidified with polyoxyethylene, polysorbate 80, nicotinamide, polyethoxylated sorbitan monolaurate and the ethyl ester of castor oil fatty acid.

In addition, the stabilizer encompasses sodium sulfite, sodium metasulfite and ether, while the preserving agent encompasses methyl p-hydroxybenzoate, ethyl p-hydroxybenzoate, sorbic acid, phenol, cresol and chlorocresol.

The present invention also relates to the use of a compound of the formula (1) of the invention for the preparation of a medicament for the prevention or treatment dyslipidaemia, atherosclerosis and diabetes.

The effective administration doses and posologies of the compounds of the invention, intended for the prevention or treatment of a disease, condition or state caused by or associated with modulation of the activity of the PPARs, depends on a large number of factors, for example on the nature of the agonist, the size of the patient, the desired aim of the treatment, the nature of the pathology to be treated, the specific pharmaceutical composition used and the observations and conclusions of the treating doctor.

For example, in the case of an oral administration, for example, a tablet or a gel capsule, a possible suitable dosage of the compounds of the formula (1) is between about 0.1 mg/kg and about 100 mg/kg of body weight per day, preferably between about 0.5 mg/kg and about 50 mg/kg of body weight per day, more preferentially between about 1 mg/kg and about 10 mg/kg of body weight per day and more preferably between about 2 mg/kg and about 5 mg/kg of body weight per day of active material.

If representative body weights of 10 kg and 100 kg are considered in order to illustrate the daily oral dosage range that can be used and as described above, suitable dosages of the compounds of the formula (1) will be between about 1-10 mg and 1000-10 000 mg per day, preferably between about 5-50 mg and 500-5000 mg per day, more preferably between about 10.0-100.0 mg and 100.0-1000.0 mg per day and even more preferentially between about 20.0-200.0 mg and about 50.0-500.0 mg per day of active material comprising a preferred compound.

These dosage ranges represent total amounts of active material per day for a given patient. The number of administrations per day at which a dose is administered may vary within wide proportions as a function of pharmacokinetic and pharmacological factors, such as the half-life of the active material, which reflects its rate of catabolism and of clearance, and also the minimum and optimum levels of the said active material reached in the blood plasma or other bodily fluids of the patient and which are required for therapeutic efficacy.

Many other factors should also be considered in deciding upon the number of daily administrations and the amount of active material that should be administered at a time. Among these other factors, and not the least of which, is the individual response of the patient to be treated.

The present invention also relates to a general process for the preparation of the compounds of the formula (1) from a compound of the formula (2):

(2)

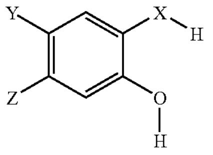

in which X, Y and Z are as defined above, the function X—H of which is subjected to the action of a compound of the formula (3):

$Hal\text{-}R^2$ (3)

in which Hal represents a halogen atom, advantageously bromine or iodine, in the presence of a base, such as an alkali metal carbonate, for example potassium carbonate or caesium carbonate, optionally in the presence of an activator, such as an alkali metal halide, for example potassium iodide, in polar aprotic medium, for example in dimethylformamide (DMF) solvent, optionally in the presence of a co-solvent, for example acetone, to give the compound of the formula (4):

(4)

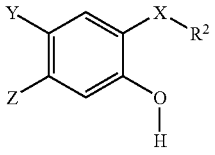

in which $R^2$, X, Y and Z are as defined above, which compound of the formula (4) is subjected, under similar conditions (for example $K_2CO_3$/KI or $Cs_2CO_3$), to the action of a halide of the formula (5):

(5)

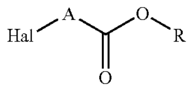

in which Hal represents a halogen atom, advantageously bromine or iodine, and R represents a protecting group for the acid function, for example an alkyl, to give the compound of the formula (6).

(6)

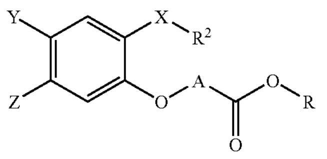

in which R, $R^2$, X, Y and Z are as defined above, the protecting group R of which is then removed, according to the standard techniques known to those skilled in the art, to give the acid of the formula ($1_{OH}$):

($1_{OH}$)

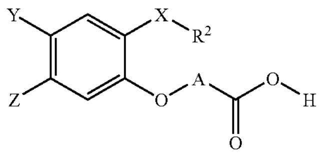

which is a special case of the compounds of the formula (1) in which $R^1$ represents a hydroxyl radical, and the acid is optionally esterified, or converted into the corresponding amide, also according to standard techniques, to give the set of compounds of the formula (1) with $R^1$ other than a hydroxyl radical.

It should be understood that the compounds of the formula (6) above, if R represents an alkyl radical, form part of the compounds of the formula (1) according to the present invention.

If such compounds are desired, the steps of deprotection of the acid and then of esterification are superfluous.

According to one variant, the compounds of the formula (1) for which X represents a sulfur atom are advantageously prepared from a compound of the formula (7):

(7)

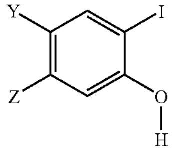

in which Y and Z are as defined above, subjected to the action of the compound of the formula (5) defined above, under conditions similar to those for obtaining the compound of the formula (6), to give the compound of the formula (8):

(8)

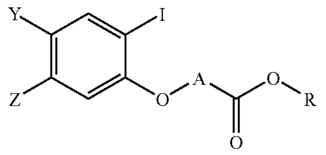

in which A, R, Y and Z are as defined above, in which compound of the formula (8) the iodine atom is substituted, under the action of a silanethiol, for example a trialkylsilanethiol, such as triisopropylsilanethiol [$(iPr)_3SiSH$], in the presence of a strong base, for example sodium hydride, and a catalyst, such as palladium(0), to give the compound of the formula (9):

(9)

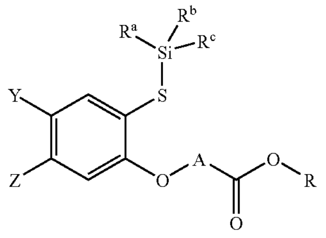

in which A, R, Y and Z are as defined above, and $R^a$, $R^b$ and $R^c$ represent the alkyl radicals of the trialkylsilanethiol, the silyl group then being removed, according to techniques known to those skilled in the art, for example using tetrabutylammonium fluoride in tetrahydrofuran, to give the compound of the formula (10):

(10)

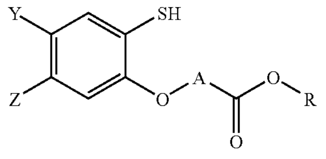

in which A, R, Y and Z are as defined above, the thiol function (—SH) of which is treated with a compound of the formula (3) defined above, according to a procedure similar to that used to obtain the compound of the formula (4), in order to give the compound of the formula (6) defined above, in which X represents a sulfur atom.

According to another variant, preferably if Y and Z do not together form a ring, and advantageously if Y and/or Z contain functions capable of reacting under the conditions for introducing the radicals $R^2$ and/or A-C(═O)O—R, the compounds of the formula (1) may also be obtained from a compound of the formula (2'):

(2')

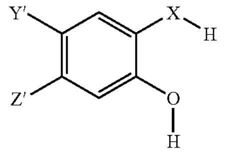

in which X is as defined above, and Y' and Z' are precursor groups of is the groups Y and Z, respectively, which are not capable of reacting under the conditions for introducing the radicals $R^2$ and/or A-C(═O)O—R, which compound of the formula (2') is used in the reactions for the synthesis of the compounds of the formulae (4) and (6) defined above, in order to give the compound of the formula (6'):

(6')

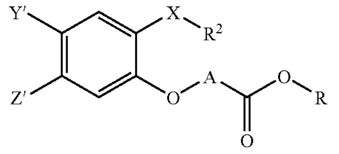

in which R, $R^2$, X, Y' and Z' are as defined above, the groups and Y' and Z' of which are then converted into groups of the formulae Y and Z, respectively, according to techniques known to those skilled in the art (for example Y' or Z' represents an alkoxycarbonyl radical and Y and Z represent a group —C(O)—$NHR^3$ or —C(O)—$NR^3R^4$), to give the compound of the formula (6) defined above.

The compounds of the formula (1) in which $R^1$ represents OH can advantageously be obtained by saponification of the corresponding compounds of the formula (1) in which $R^1$ represents an alkoxy radical, or alternatively starting with the compounds of the formula (6), in which R represents an alkyl radical. The saponification can be performed via the action of a base, such as a mineral base chosen from lithium hydroxide, potassium hydroxide, sodium hydroxide, sodium hydrogen carbonate, potassium hydrogen carbonate, sodium carbonate and potassium carbonate. The molar amount of base to be used generally ranges from 1 to 20 equivalents and preferably from 1 to 12 equivalents depending on the strength of the selected base.

The reaction is preferably performed in a solvent of polar protic type and more preferably in a mixture of a lower ($C_1$-$C_4$) alkanol and water, such as a mixture of ethanol and water or methanol and water.

The reaction temperature advantageously ranges between 35° and 120° C. and better still between 40° and 100° C., for example between 50° C. and reflux.

In the processes described above, it should be understood that the operating conditions may vary substantially as a function of the various substituents present in the compounds of the formula (1) that it is desired to prepare. Such variations and adaptations are readily accessible to those skilled in the art, for example from scientific reviews, the patent literature, Chemical Abstracts, and computer databases, including the Internet. Similarly, the starting materials are either commercially available or accessible via syntheses that a person skilled in the art can readily find, for example in the various publications and databases described above.

The optical isomers of the compounds of the formula (1) can be obtained on the one hand via standard techniques for separating and/or purifying isomers known to those skilled in the art, starting with the racemic mixture of the compound of the formula (1). The optical isomers can also be obtained directly via stereoselective synthesis of an optically active starting compound, or via separation or recrystallisation of the optically active salts of the compounds of the formula (1), the salts being obtained with chiral amines or chiral acids.

Similarly, the possible pharmaceutically acceptable addition salts with acids or bases, and the possible oxide forms, in particular the N-oxides, are readily accessible from the compounds of the formula (1) according to the operating techniques usually used in this field.

The examples that follow illustrate the present invention without limiting it in any way. In these examples and the proton nuclear magnetic resonance data (300 MHz NMR), the following abbreviations have been used: s for singlet, d for doublet, t for triplet, q for quartet, o for octet and m for complex multiplet. The chemical shifts δ are expressed in ppm.

EXAMPLES

Example 1

Methyl 3-(3-oxo-6-propylsulfanylindan-5-yloxymethyl)benzoate

Step 1

A mixture of 6-hydroxy-5-iodoindan-1-one (4.1 g; 15 mmol), methyl 3-bromomethylbenzoate (3.77 g; 16.5 mmol) and caesium carbonate (7.3 g; 22.4 mmol) in dimethylformamide (DMF) (120 ml) is heated at 65° C. for 1 hour 30 minutes. The reaction medium is poured into a mixture of water and methylene chloride. The aqueous phase is extracted with ethyl acetate. The combined organic phases are dried over sodium sulfate and then concentrated. The solid obtained is triturated with diisopropyl ether and then isolated by flash chromatography ($CH_2Cl_2$) (4.59 g; 73% yield).

$^1H$ NMR (300 MHz, DMSO-D6) δ ppm: 2.6 (m, 2 H) 3.0 (m, 2 H) 3.9 (s, 3 H) 5.4 (s, 2 H) 7.2 (s, 1 H) 7.6 (m, 1 H) 7.8 (d, J=7.6 Hz, 1 H) 7.9 (d, J=7.8 Hz, 1 H) 8.1 (m, 2 H).

Step 2

A suspension of sodium hydride (NaH) at 60% in oil (0.242 g; 6.05 mmol) in tetrahydrofuran (THF) (10 ml) is cooled to 0° C. under nitrogen. Triisopropylsilanethiol (1.125 g; 5.91 mmol) is then added dropwise and the medium is stirred for 30 minutes at room temperature. $Pd(PPh_3)_4$ (0.55 g; 0.48 mmol) and then a solution of the compound obtained in step 1 (2.5 g; 5.92 mmol) in toluene (50 ml) are then added quickly and the medium is heated at 80° C. for 2 hours 30 minutes.

The mixture is poured into water and extracted with ethyl ether. The combined organic phases are dried over sodium sulfate and then concentrated (oil; 3.9 g). After dispersing in pentane, followed by flash chromatography (1/1 heptane/ethyl acetate), the expected product is obtained (1.6 g; 56% yield).

$^1H$ NMR (300 MHz, chloroform-D) δ ppm: 1.2 (m, 18 H) 1.4 (m, 3 H) 2.8 (m, 2 H) 3.1 (m, 2 H) 4.0 (s, 3 H) 5.3 (s, 2 H) 7.5 (m, 2 H) 7.8 (m, 2 H) 8.2 (m, 2 H)

Step 3

A mixture of the silyl derivative from step 2 above (1.6 g; 3.3 mmol) in 1N tetra-n-butylammonium fluoride solution ($nBu_4NF$; 3.6 ml; 3.6 mmol) is stirred at room temperature for 30 minutes. The medium is poured into dilute hydrochloric acid, extracted with ethyl ether, dried over sodium sulfate and concentrated. The semi-crystalline product obtained is dispersed in diisopropyl ether (0.69 g; 64% yield).

$^1H$ NMR (300 MHz, chloroform-D) δ ppm: 2.7 (m, 2 H) 3.0 (m, 2 H) 3.9 (s, 3 H) 4.2 (s, 1 H) 5.2 (s, 2 H) 7.2 (s, 1 H) 7.4 (s, 1 H) 7.5 (m, 1 H) 7.7 (d, J=7.6 Hz, 1 H) 8.0 (d, J=7.8 Hz, 1 H) 8.1 (s, 1 H)

Step 4

A mixture of the compound obtained in step 3 (100 mg; 0.305 mmol), 3-bromopropane (41.3 mg; 0.336 mmol) and caesium carbonate (104.3 mg; 0.32 mmol) in acetone (1 ml) and DMF (1.5 ml) is heated at 60° C. for 3 hours. The medium is poured into water, extracted with ethyl ether, dried over sodium sulfate and concentrated (0.12 g; quantitative yield).

$^1H$ NMR (300 MHz, chloroform-D) δ ppm: 1.1 (t, J=7.3 Hz, 3 H) 1.8 (m, 2 H) 2.7 (m, 2 H) 3.0 (t, J=7.3 Hz, 2 H) 3.1 (m, 2 H) 3.9 (s, 3 H) 5.2 (s, 2H) 7.2 (s, 1 H) 7.2 (s, 1 H) 7.5 (m, 1 H) 7.7 (d, J=7.8 Hz, 1 H) 8.0 (d, J=7.8 Hz, 1 H) 8.1 (s, 1 H).

Example 2

3-(3-Oxo-6-propylsulfanylindan-5-yloxymethyl)benzoic Acid

A mixture of the compound of Example 1 (0.12 g; 0.3 mmol), methanol (25 ml), sodium hydroxide (NaOH; 51.84 mg; 1.3 mmol) and water (5 ml) is heated at 80° C. for two hours. The solvents are evaporated off. The residue is dissolved in water and treated with concentrated hydrochloric acid (HCl). After extracting with methylene chloride and drying over sodium sulfate, the evaporation residue is dispersed in ethyl ether (41 mg; 38% yield).

$^1H$ NMR (300 MHz, DMSO-D6) δ ppm: 1.0 (t, J=7.3 Hz, 3 H) 1.7 (m, 2 H) 2.6 (m, 2 H) 3.0 (t, J=7.2 Hz, 4 H) 5.3 (s, 2 H) 7.2 (s, 1 H) 7.4 (s, 1 H) 7.5 (t, J=7.7 Hz, 1 H) 7.7 (d, J=7.7 Hz, 1 H) 7.9 (m, 1 H) 8.1 (s, 1 H) 13.0 (s, 1 H).

Mass: ES-355.3.

Example 3

Methyl 3-(3-oxo-6-pentyloxyindan-5-yloxymethyl)benzoate

Step 1

A mixture of 5,6-dihydroxyindanone (2.2 g; 13.4 mmol), iodopentane (1.75 ml; 13.4 mmol) and caesium carbonate ($Cs_2CO_3$; 4.8 g; 14.7 mmol) in DMF (50 ml) is heated at 40° C. for 35 minutes. The medium is cooled to room temperature, poured into water and extracted with methylene chloride. The combined organic phases are washed with water, dried over sodium sulfate and then concentrated (1.9 g solid). Flash chromatography (85/15 heptane/ethyl acetate) gives the expected product (1.5 g; 48% yield).

Melting point=110-111° C.

$^1H$ NMR (300 MHz, chloroform-D) δ ppm: 0.9 (m, 3 H) 1.4 (m, 4 H) 1.9 (m, 2 H) 2.6 (m, 2 H) 3.0 (m, 2 H) 4.1 (t, J=6.6 Hz, 2 H) 5.8 (m, 1 H) 6.9 (s, 1 H) 7.3 (m, 1 H).

Step 2

A mixture of the compound obtained in step 1 (2.0 g; 8.53 mmol), methyl 3-bromomethylbenzoate (2.9 g; 12.66 mmol), potassium iodide (0.3 g; 1.8 mmol) and potassium carbonate (1.75 g; 12.7 mmol) in DMF (50 ml) is heated at 80° C. for 2 hours. A further 50 ml of DMF are added and the mixture is refluxed for 2 hours. The solvent is evaporated off and the solid residue is taken up in water and then extracted with ethyl acetate. The combined organic phases are washed with brine, dried over sodium sulfate and then concentrated (3.4 g solid). The solid is taken up in diisopropyl ether at elevated temperature, for crystallisation (1.7 g; melting point=127° C.). An insoluble material is filtered off while hot and is purified by chromatography on silica (7/3 heptane/ethyl acetate). A further 0.6 g of the expected product is obtained (melting point=127° C.). The total yield is 71%.

$^1$H NMR (300 MHz, chloroform-D) δ ppm: 0.9 (t, J=7.1 Hz, 3 H) 1.5 (m, 4 H) 1.9 (dd, J=14.3, 6.7 Hz, 2 H) 2.7 (m, 2 H) 3.0 (m, 2 H) 3.9 (s, 3 H) 4.1 (t, J=6.6 Hz, 2 H) 5.2 (s, 2 H) 6.9 (s, 1 H) 7.2 (s, 1 H) 7.4 (m, Hz, 1 H) 7.7 (d, J=7.6 Hz, 1 H) 8.0 (d, J=7.6 Hz, 1 H) 8.1 (s, 1 H).

Example 4

3-(3-Oxo-6-pentyloxyindan-5-yloxymethyl)benzoic Acid

A mixture of the compound obtained in Example 3 (2.3 g; 6.01 mmol), methanol (330 ml), sodium hydroxide (0.96 g; 24 mmol) and water (24 ml) is refluxed for 3 hours. The medium is concentrated to dryness. The residue is taken up in water. The basic aqueous phase is washed with ethyl ether and then acidified with 1N HCl. The cream-coloured precipitate formed is dissolved in methylene chloride. The organic phase is washed with water, dried over sodium sulfate and concentrated (1.5 g; 68% yield).

Melting point=190° C.

$^1$H NMR (300 MHz, DMSO-D6) δ ppm: 0.9 (t, J=7.2 Hz, 3 H) 1.4 (m, 4 H) 1.8 (m, 2 H) 2.6 (m, 2 H) 3.0 (m, 2 H) 4.1 (t, J=6.4 Hz, 2 H) 5.2 (s, 2 H) 7.1 (s, 1 H) 7.2 (s, 1 H) 7.5 (m, J=7.7, 7.7 Hz, 1 H) 7.7 (d, J=7.6 Hz, 1 H) 7.9 (m, 1 H) 8.1 (s, 1 H) 13.0 (s, 1 H).

Mass LC/MS ES+367.4.

Example 5 t-Butyl 3-[5-(morpholine-4-carbonyl)-2-pentyloxyphenoxymethyl]-benzoate

Step 1

A mixture of methyl 3,4-dihydroxybenzoate (8.74 g; 52 mmol), iodopentane (10.3 g; 52 mmol) and caesium carbonate (20.33 g; 62 mmol) in dimethylformamide (200 ml) is heated at 30° C. for 1 hour. The mixture is poured into water and is then extracted with ethyl ether. The ether phase is dried over sodium sulfate and then concentrated to dryness. The evaporation residue (14 g) is purified by flash chromatography on silica (5/1 heptane/ethyl acetate). The expected product is obtained in solid form (4.3 g; 35% yield).

$^1$H NMR (300 MHz, DMSO-D6) δ ppm: 0.9 (t, J=7.1 Hz, 3 H) 1.4 (m, 4 H) 1.7 (dd, J=14.3, 6.9 Hz, 2 H) 3.8 (s, 3 H) 4.0 (t, J=6.6 Hz, 2 H) 7.0 (d, J=8.4 Hz, 1 H) 7.4 (m, 2 H) 9.3 (s, 1 H).

Step 2

A mixture of the product obtained in step 1 (4.4 g; 18.47 mmol), t-butyl 3-chloromethylbenzoate (4.18 g; 18.44 mmol) and caesium carbonate (9.02 g; 27.68 mmol) in DMF (150 ml) is heated at 60-65° C. for 3 hours. The mixture is poured into water and then extracted with ethyl ether. The ether phase is dried over sodium sulfate and then concentrated to dryness. The evaporation residue (8.5 g) is purified by flash chromatography on alumina (3/1 heptane/ethyl acetate). The expected product is obtained in oil form (7.47 g; 94% yield).

$^1$H NMR (300 MHz, DMSO-D6) δ ppm: 0.9 (t, J=7.0 Hz, 3 H) 1.4 (m, 4 H) 1.5 (s, 9 H) 1.7 (m, 2 H) 3.8 (s, 3 H) 4.1 (t, J=6.4 Hz, 2 H) 5.2 (s, 2 H) 7.1 (d, J=8.4 Hz, 1 H) 7.6 (m, 3 H) 7.7 (d, J=7.4 Hz, 1 H) 7.9 (d, J=7.8 Hz, 1 H) 8.0 (s, 1 H).

Step 3

A mixture of the product obtained in step 2 (7.47 g; 17.43 mmol), sodium hydroxide (2.79 g; 69.76 mmol), methanol (130 ml) and water (33 ml) is heated at 60° C. for 2 hours. The solvents are evaporated to dryness. The residue is taken up in water and the pH is adjusted to pH 3 with dilute hydrochloric acid. The mixture is extracted with ethyl ether. The ether phase is dried over sodium sulfate and then concentrated to dryness. The expected product is obtained in solid form (5.32 g; 62% yield).

LC/MS ES-413.4

Step 4

To a solution in THF of the compound obtained in step 3 (0.502 g; 1.21 mmol) is added carbonyldiimidazole (0.274 g; 1.69 mmol). The reaction medium is stirred for 2 hours at room temperature. Morpholine (0.105 g; 1.21 mmol) is then added and the mixture is stirred for 4 hours at 60° C. The mixture is poured into water and then extracted with ethyl ether. The ether phase is dried over sodium sulfate and then concentrated to dryness. The evaporation residue (0.42 g) is purified by flash chromatography on silica (1/1 dichloromethane/ethyl acetate). The expected product is obtained in oil form (0.17 g; 29% yield).

$^1$H NMR (300 MHz, chloroform-D) δ ppm: 0.9 (t, J=7.0 Hz, 3 H) 1.4 (d, J=6.5 Hz, 4 H) 1.6 (s, 9 H) 1.8 (dd, J=14.2, 6.8 Hz, 2 H) 3.6 (m, 8 H) 4.0 (t, J=6.7 Hz, 2 H) 5.2 (s, 2 H) 6.9 (d, J=8.2 Hz, 1 H) 7.0 (d, J=1.7 Hz, 1 H) 7.0 (m, 1 H) 7.4 (t, J=7.6 Hz, 1 H) 7.6 (d, J=7.2 Hz, 1 H) 7.9 (d, J=7.6 Hz, 1 H) 8.0 (s, 1 H).

Example 6

3-[5-(Morpholine-4-carbonyl)-2-pentyloxyphenoxymethyl]benzoic Acid

To a solution of the compound obtained in Example 5 (0.17 g; 0.35 mmol) in dichloromethane (17 ml) is added trifluoroacetic acid (3.4 ml) and the medium is stirred at room temperature for 2 hours. After evaporating to dryness, the residue is crystallized from pentane. The powder is filtered off by suction and dried (0.14 g; 93% yield).

$^1$H NMR (300 MHz, DMSO-D6) δ ppm: 0.9 (t, J=7.1 Hz, 3 H) 1.4 (m, 4H) 1.7 (m, 2 H) 3.5 (m, 8 H) 4.0 (t, J=6.4 Hz, 2 H) 5.2 (s, 2 H) 7.0 (m, 3 H) 7.5 (m, 1 H) 7.7 (d, J=7.4 Hz, 1 H) 7.9 (d, J=7.8 Hz, 1 H) 8.0 (s, 1 H) 12.9 (s, 1 H).

Mass LC/MS ES+428.3.

Compounds 7 to 64 were prepared according to protocols similar to those described for the preparation of the compounds of Examples 1 to 6 above.

The structures of compounds 7 to 64 are collated in Table 1 below:

TABLE 1
Structure of compounds 7 to 64
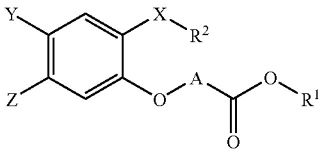
| Ex. | $R^1$ | A | $R^2$ | X | Y | Z |
|---|---|---|---|---|---|---|
| 7 | —H | $-(CH_2)_3-$ | $-(CH_2)_5-CH_3$ | —O— | | 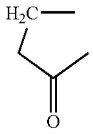 |
| 8 | —H | $-CH_2-$ | $-(CH_2)_5-CH_3$ | —O— | | 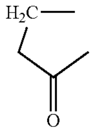 |
| 9 | —H | $-(CH_2)_3-$ | $-(CH_2)_4-CH_3$ | —O— | | 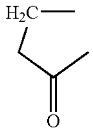 |
| 10 | —H | $-CH_2-$ | $-(CH_2)_4-CH_3$ | —O— | | 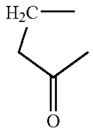 |
| 11 | —H | $-C(CH_3)_2-$ | $-(CH_2)_4-CH_3$ | —O— | | 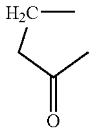 |
| 12 | —H | 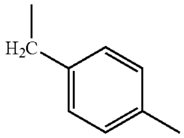 | $-(CH_2)_4-CH_3$ | —O— | | 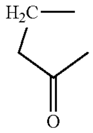 |
| 13 | —H | $-(CH_2)_3-$ | 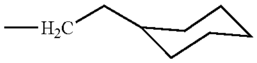 | —O— | | 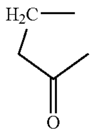 |
| 14 | —H | $-C(CH_3)_2-$ | 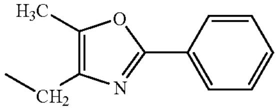 | —O— | | 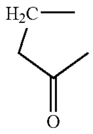 |
| 15 | —H | $-(CH_2)_3-$ | 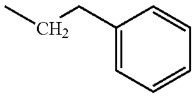 | —O— | | 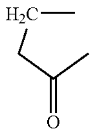 |

TABLE 1-continued
Structure of compounds 7 to 64
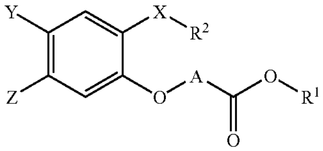
| Ex. | $R^1$ | A | $R^2$ | X | Y | Z |
|---|---|---|---|---|---|---|
| 16 | —H | —$C(CH_3)_2$— | 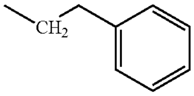 | —O— | | 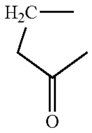 |
| 17 | —H | 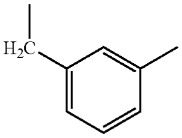 | 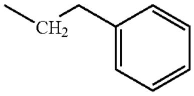 | —O— | | 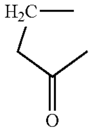 |
| 18 | —H | 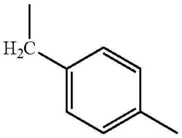 | 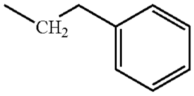 | —O— | | 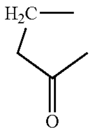 |
| 19 | —H | —$(CH_2)_3$— | 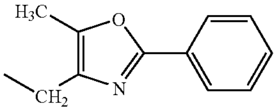 | —O— | | 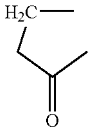 |
| 20 | —H | 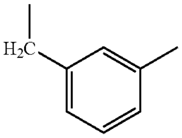 | 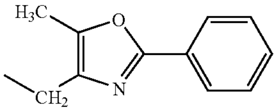 | —O— | | 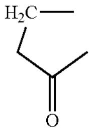 |
| 21 | —H | 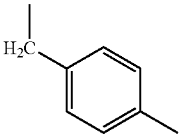 | 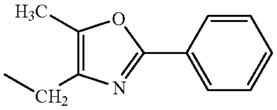 | —O— | | 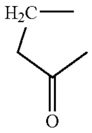 |
| 22 | —H | —$CH_2$— | 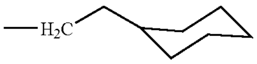 | —O— | | 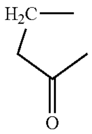 |
| 23 | —H | —$C(CH_3)_2$— | 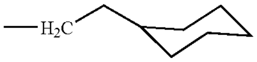 | —O— | | 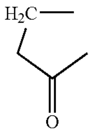 |
| 24 | —H | —$(CH_2)_3$— | 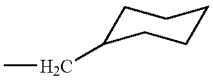 | —O— | | 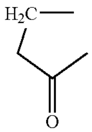 |

TABLE 1-continued
Structure of compounds 7 to 64
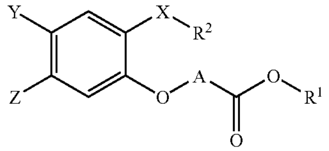
| Ex. | $R^1$ | A | $R^2$ | X | Y | Z |
|---|---|---|---|---|---|---|
| 25 | —H | —$C(CH_3)_2$— | 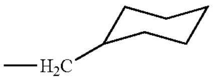 | —O— | | 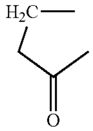 |
| 26 | —H | —$(CH_2)_3$— | 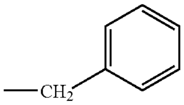 | —O— | | 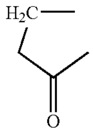 |
| 27 | —H | —$C(CH_3)_2$— | 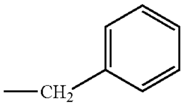 | —O— | | 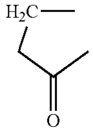 |
| 28 | —H | 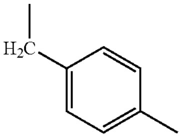 | 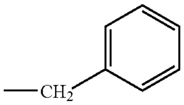 | —O— | | 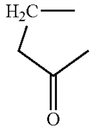 |
| 29 | —H | —$(CH_2)_3$— | 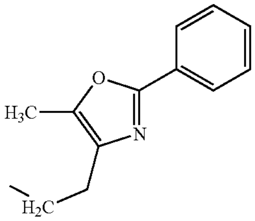 | —O— | | 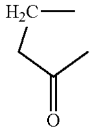 |
| 30 | —H | —$C(CH_3)_2$— | 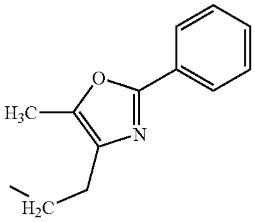 | —O— | | 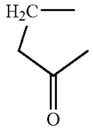 |
| 31 | —H | 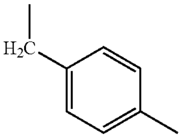 | 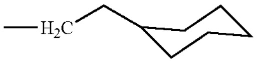 | —O— | | 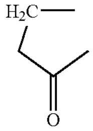 |
| 32 | —H | 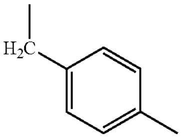 | 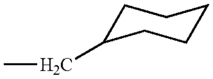 | —O— | | 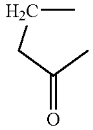 |

TABLE 1-continued
Structure of compounds 7 to 64
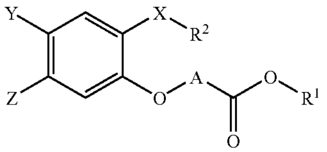
| Ex. | $R^1$ | A | $R^2$ | X | Y | Z |
|---|---|---|---|---|---|---|
| 33 | —H | —$CH_2$— | 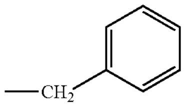 | —O— | | 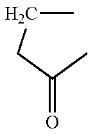 |
| 34 | —H | —$CH_2$— | 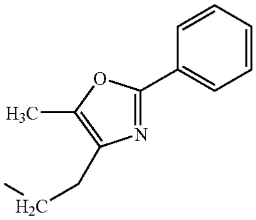 | —O— | | 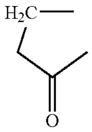 |
| 35 | —H | 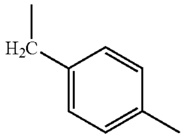 | 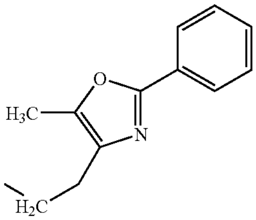 | —O— | | 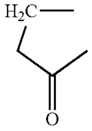 |
| 36 | —H | 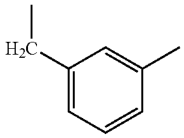 | —$(CH_2)_4$—$CH_3$ | —O— | —H | 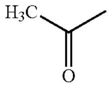 |
| 37 | —H | 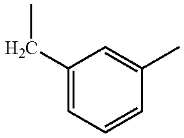 | 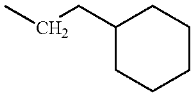 | —O— | —H | 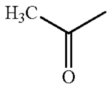 |
| 38 | —H | 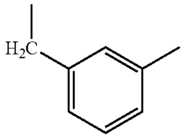 | 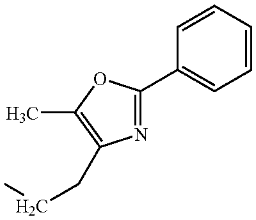 | —O— | —H | 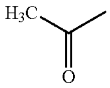 |
| 39 | —H | 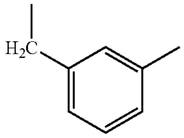 | —$(CH_2)_4$—$CH_3$ | —S— | | 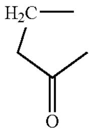 |

TABLE 1-continued
Structure of compounds 7 to 64
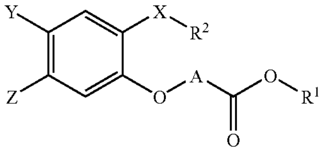
| Ex. | $R^1$ | A | $R^2$ | X | Y | Z |
|---|---|---|---|---|---|---|
| 40 | —H | 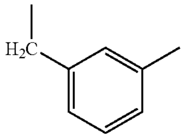 | 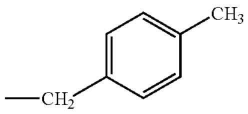 | —S— | | 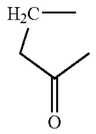 |
| 41 | —H | 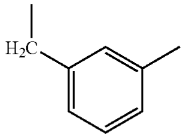 | 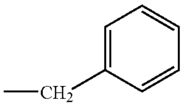 | —O— | —H | —H |
| 42 | —H | 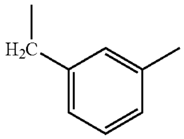 | 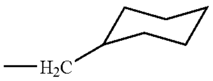 | —O— | | 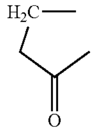 |
| 43 | —H | 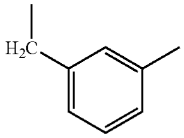 | 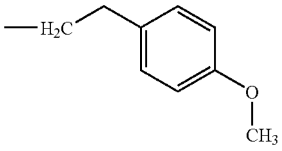 | —S— | | 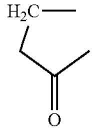 |
| 44 | —H | 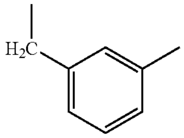 | 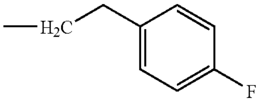 | —S— | | 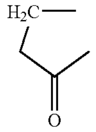 |
| 45 | —H | 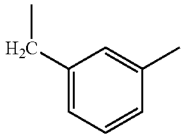 | 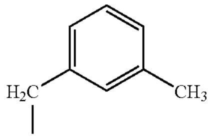 | —S— | | 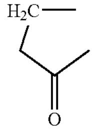 |
| 46 | —H | 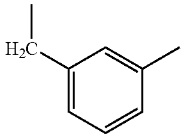 | 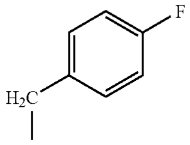 | —S— | | 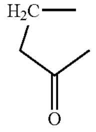 |
| 47 | —H | 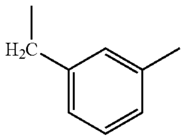 | $-(CH_2)_4-CH_3$ | —O— | —H | —H |
| 48 | —H | 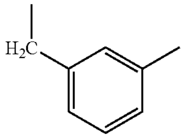 | 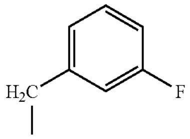 | —S— | | 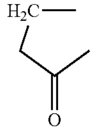 |

TABLE 1-continued
Structure of compounds 7 to 64
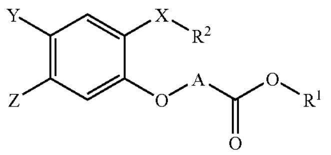
| Ex. | $R^1$ | A | $R^2$ | X | Y | Z |
|---|---|---|---|---|---|---|
| 49 | —H | 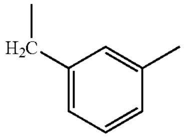 | $—(CH_2)_3—CH_3$ | —S— | | 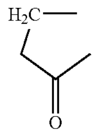 |
| 50 | —H | 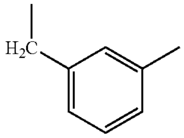 | 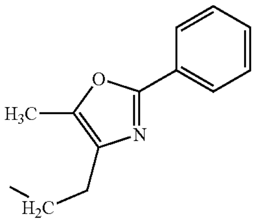 | —O— | —H | —H |
| 51 | —H | 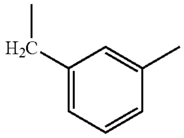 | 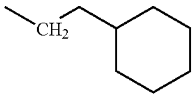 | —O— | —H | —H |
| 52 | —H | 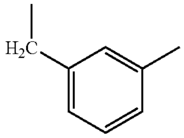 | $—CH_3$ | —O— | —H | 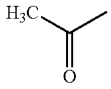 |
| 53 | —H | 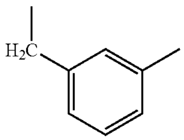 | $—(CH_2)_2—CH_3$ | —O— | —H | 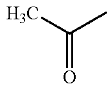 |
| 54 | —H | 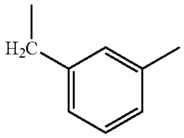 | $—(CH_2)_4—CH_3$ | —O— | —H | 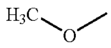 |
| 55 | —H | 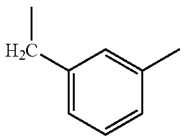 | 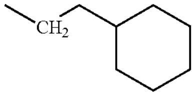 | —O— | —H | 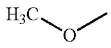 |
| 56 | —H | 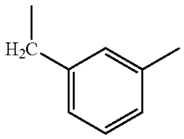 | $—(CH_2)_4—CH_3$ | —O— | —H | 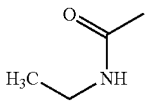 |

TABLE 1-continued
Structure of compounds 7 to 64
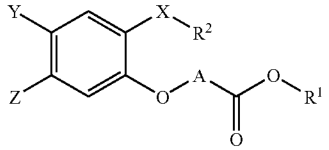
| Ex. | $R^1$ | A | $R^2$ | X | Y | Z |
|---|---|---|---|---|---|---|
| 57 | —H | 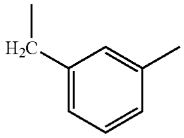 | —$(CH_2)_4$—$CH_3$ | —O— | —H | 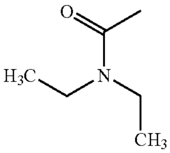 |
| 58 | —H | 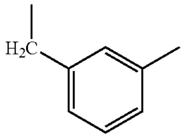 | —$(CH_2)_4$—$CH_3$ | —O— | —H | 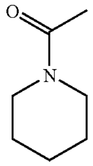 |
| 59 | —H | 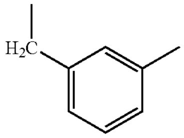 | 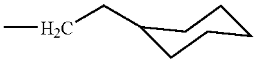 | —O— | | 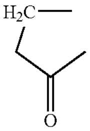 |
| 60 | —H | 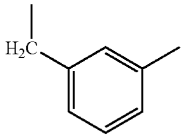 | —$(CH_2)_4$—$CH_3$ | —O— | —H | 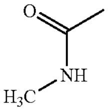 |
| 61 | —H | 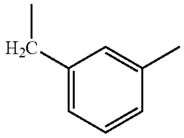 | 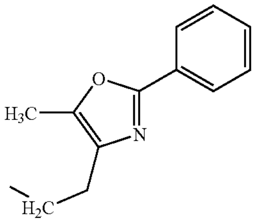 | —O— | —H | —H |
| 62 | —H | 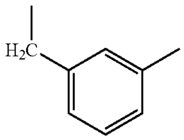 | 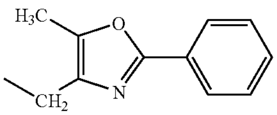 | —O— | —H | 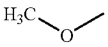 |
| 63 | —H | 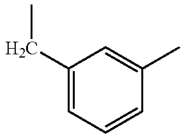 | —$(CH_2)_4$—$CH_3$ | —O— | —H | 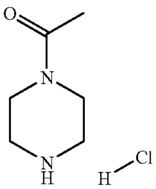 |

TABLE 1-continued

Structure of compounds 7 to 64

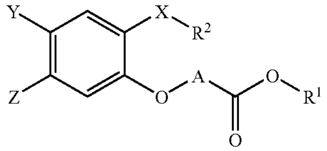

| Ex. | $R^1$ | A | $R^2$ | X | Y | Z |
|---|---|---|---|---|---|---|
| 64 | —H | 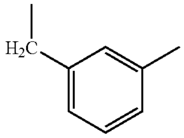 | 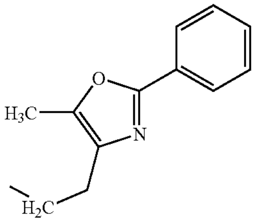 | —O— | —H | 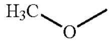 |

The results of the analyses of the synthesized products 6 to 31 are given in Table 2 below, in which table:

M represents the theoretical molar mass of the compound;

m.p. represents the melting point in ° C.;

LC/MS indicates the result of the analysis by mass spectrometry coupled to liquid-phase chromatography; and NMR indicates the chemical shifts δ (in ppm) of the proton by magnetic resonance at 300 MHz.

TABLE 2

| Ex. No. | M | M.p. | LCMS | NMR |
|---|---|---|---|---|
| 7 | 334.41 | | ES− 333.4 | $^1$H NMR (300 MHz, chloroform-D) δ ppm 0.9 (t, J = 6.9 Hz, 3 H) 1.4 (m, 6 H) 1.9 (m, 2 H) 2.2 (m, 2 H) 2.6 (m, 4 H) 3.0 (m, 2 H) 4.1 (t, 4 H) 6.9 (s, 1 H) 7.2 (s, 1 H) |
| 8 | 306.36 | | | $^1$H NMR (300 MHz, chloroform-D) δ ppm 0.9 (m, 3 H) 1.4 (m, 6 H) 1.9 (m, 2 H) 2.7 (m, 2 H) 3.0 (m, 2 H) 4.1 (t, J = 6.8 Hz, 2 H) 4.7 (s, 2 H) 5.2 (s, 1 H) 6.9 (s, 1 H) 7.3 (s, 1 H) |
| 9 | 320.38 | | ES+ 321.3 | $^1$H NMR (300 MHz, chloroform-D) δ ppm 0.9 (t, J = 7.1 Hz, 3 H) 1.4 (m, 4 H) 1.9 (m, 2 H) 2.2 (m, 2 H) 2.6 (m, 4 H) 3.0 (m, 2 H) 4.1 (m, 4 H) 6.9 (s, 1 H) 7.2 (s, 1 H) |
| 10 | 292.33 | | | $^1$H NMR (300 MHz, chloroform-D) δ ppm 0.9 (t, J = 7.1 Hz, 3 H) 1.4 (m, 4 H) 1.9 (m, 2 H) 2.7 (m, 2 H) 3.0 (m, 2 H) 4.1 (t, J = 6.8 Hz, 2 H) 4.7 (s, 2 H) 5.7 (s, 1 H) 6.9 (s, 1 H) 7.3 (s, 1 H) |
| 11 | 320.38 | | ES+ 321.2 ES− 319.2 | $^1$H NMR (300 MHz, benzene-D6) δ ppm 0.9 (m, 3 H) 1.4 (m, 4 H) 1.5 (s, 6 H) 1.9 (m, 2 H) 2.7 (m, 2 H) 3.1 (m, 2 H) 4.1 (t, J = 6.8 Hz, 2 H) 7.0 (s, 1 H) 7.4 (s, 1 H) |
| 12 | 368.43 | | | $^1$H NMR (300 MHz, DMSO-D6) δ ppm 0.9 (t, J = 6.9 Hz, 3 H) 1.4 (m, 4 H) 1.8 (m, 2 H) 2.5 (d, J = 1.7 Hz, 2 H) 3.0 (m, 2 H) 4.1 (t, J = 6.4 Hz, 2 H) 5.3 (s, 2 H) 7.1 (s, 1 H) 7.2 (s, 1 H) 7.6 (d, J = 8.0 Hz, 2 H) 7.9 (d, J = 8.0 Hz, 2 H) 13.0 (s, 1 H) |
| 13 | 360.45 | | ES− 359.2 | |
| 14 | 421.45 | | ES+ 422.3 ES− 420.3 | $^1$H NMR (300 MHz, chloroform-D) δ ppm 1.5 (s, 6 H) 2.4 (s, 3 H) 2.6 (m, 2 H) 3.0 (m, 2 H) 5.0 (s, 2 H) 7.2 (s, 1 H) 7.3 (s, 1 H) 7.4 (dd, J = 6.8, 3.7 Hz, 3 H) 7.9 (m, 2 H) |
| 15 | 354.40 | | ES+ 355.2 ES− 353.3 | $^1$H NMR (300 MHz, chloroform-D) δ ppm 2.2 (m, 2 H) 2.6 (m, 4 H) 3.0 (m, 2 H) 3.2 (t, J = 7.0 Hz, 2 H) 4.1 (t, J = 6.0 Hz, 2 H) 4.3 (t, J = 7.0 Hz, 2 H) 6.9 (s, 1 H) 7.2 (s, 1 H) 7.3 (m, 5 H) |
| 16 | 354.40 | | ES− 353.3 | $^1$H NMR (300 MHz, chloroform-D) δ ppm 1.4 (s, 6 H) 2.6 (m, 2 H) 3.0 (m, 2 H) 3.1 (t, J = 7.2 Hz, 2 H) 4.3 (t, J = 7.2 Hz, 2 H) 6.9 (s, 1 H) 7.2 (m, 6 H) |

TABLE 2-continued

| Ex. No. | M | M.p. | LCMS | NMR |
|---|---|---|---|---|
| 17 | 402.44 | | ES− 401.3 | $^1$H NMR (300 MHz, DMSO-D6) δ ppm 2.5 (m, 2 H) 3.1 (m, 4 H) 4.3 (t, J = 6.6 Hz, 2 H) 5.2 (s, 2 H) 7.3 (m, 7 H) 7.5 (t, J = 7.6 Hz, 1 H) 7.7 (d, J = 7.4 Hz, 1 H) 7.9 (d, J = 7.6 Hz, 1 H) 8.1 (s, 1 H) 13.0 (s, 1 H) |
| 18 | 402.44 | | ES− 401.2 | $^1$H NMR (300 MHz, DMSO-D6) δ ppm 2.5 (m, 2 H) 3.0 (m, 2 H) 3.1 (t, J = 6.5 Hz, 2 H) 4.3 (t, J = 6.5 Hz, 2 H) 5.2 (s, 2 H) 7.1 (s, 1 H) 7.3 (m, 4 H) 7.4 (m, 2 H) 7.5 (d, J = 8.2 Hz, 2 H) 8.0 (d, J = 8.2 Hz, 2 H) 13.0 (s, 1 H) |
| 19 | 421.45 | | ES+ 422.3 | $^1$H NMR (300 MHz, chloroform-D) δ ppm 2.3 (s, 2 H) 2.4 (dd, J = 9.1, 2.8 Hz, 2 H) 2.5 (s, 3 H) 2.7 (m, 2 H) 3.1 (t, 2 H) 4.1 (t, J = 5.2 Hz, 2 H) 5.0 (s, 2 H) 7.0 (s, 1 H) 7.2 (s, 1 H) 7.5 (m, 3 H) 8.0 (m, 2 H) |
| 20 | 469.49 | | ES− 468.3 | $^1$H NMR (300 MHz, DMSO-D6) δ ppm 2.5 (s, 3 H) 2.6 (m, 2 H) 3.0 (m, 2 H) 5.2 (s, 2 H) 5.3 (s, 2 H) 7.2 (s, 1 H) 7.4 (s, 1 H) 7.5 (m, 4 H) 7.7 (d, J = 7.8 Hz, 1 H) 7.9 (d, J = 7.8 Hz, 1 H) 7.9 (m, 2 H) 8.0 (s, 1 H) 13.0 (s, 1 H) |
| 21 | 469.49 | | ES+ 470.2 | $^1$H NMR (300 MHz, DMSO-D6) δ ppm 2.5 (s, 3 H) 2.6 (m, 2 H) 3.0 (m, 2 H) 5.2 (s, 2 H) 5.3 (s, 2 H) 7.2 (s, 1 H) 7.4 (s, 1 H) 7.5 (m, 5 H) 7.9 (m, 4 H) 12.9 (s, 1 H) |
| 22 | 332.39 | | ES+ 333.4<br>ES− 331.4 | $^1$H NMR (300 MHz, chloroform-D) δ ppm 1.0 (m, 2 H) 1.2 (m, 3 H) 1.5 (m, 1 H) 1.8 (m, 7 H) 2.7 (dd, J = 6.4, 4.5 Hz, 2 H) 3.1 (m, 2 H) 4.2 (t, J = 7.0 Hz, 2 H) 4.7 (s, 2 H) 5.0 (s, 1 H) 7.0 (s, 1 H) 7.3 (s, 1 H) |
| 23 | 360.45 | | ES+ 361.4<br>ES− 359.4 | $^1$H NMR (300 MHz, chloroform-D) δ ppm 1.1 (m, 5 H) 1.5 (m, 1 H) 1.5 (s, 6 H) 1.8 (m, 7 H) 2.8 (dd, J = 6.4, 4.7 Hz, 2 H) 3.1 (m, 2 H) 4.2 (t, J = 6.9 Hz, 2 H) 5.9 (s, 1 H) 7.0 (s, 1 H) 7.4 (s, 1 H) |
| 24 | 346.42 | | ES− 345.4 | $^1$H NMR (300 MHz, chloroform-D) δ ppm 1.2 (m, 5 H) 1.8 (m, 6 H) 2.2 (m, 2 H) 2.6 (m, 2 H) 2.7 (m, 2 H) 3.1 (m, 2 H) 3.9 (d, J = 6.0 Hz, 2 H) 4.1 (t, J = 6.0 Hz, 2 H) 5.2 (s, 1 H) 6.9 (s, 1 H) 7.2 (s, 1 H) |
| 25 | 346.42 | | ES− 345.4 | $^1$H NMR (300 MHz, chloroform-D) δ ppm 1.2 (m, 5 H) 1.5 (s, 6 H) 1.9 (m, 7 H) 2.8 (m, 2 H) 3.1 (m, 2 H) 3.9 (d, J = 6.2 Hz, 2 H) 7.0 (s, 1 H) 7.4 (s, 1 H) |
| 26 | 340.37 | | ES− 339.4 | $^1$H NMR (300 MHz, chloroform-D) δ ppm 2.1 (m, 2 H) 2.5 (t, J = 7.1 Hz, 2 H) 2.7 (m, 2 H) 3.0 (m, 2 H) 4.0 (t, J = 5.9 Hz, 2 H) 5.1 (s, 2 H) 6.9 (s, 1 H) 7.2 (s, 1 H) 7.3 (m, 5 H) 8.8 (s, 1 H) |
| 27 | 340.37 | | ES− 339.4 | $^1$H NMR (300 MHz, chloroform-D) δ ppm 1.5 (s, 6 H) 2.7 (m, 2 H) 3.1 (m, 2 H) 3.7 (s, 1 H) 5.2 (s, 2 H) 7.1 (s, 1 H) 7.4 (m, 6 H) |
| 28 | 388.42 | | ES− 387.4 | |
| 29 | 435.47 | | ES+ 436.4 | $^1$H NMR (300 MHz, chloroform-D) δ ppm 2.2 (m, 2 H) 2.6 (m, 2 H) 2.6 (s, 3 H) 2.8 (m, 2 H) 3.1 (m, 2 H) 3.3 (t, J = 5.6 Hz, 2 H) 4.1 (t, J = 5.9 Hz, 2 H) 4.4 (m, 2 H) 6.9 (s, 1 H) 7.2 (s, 1 H) 7.6 (m, 3 H) 8.1 (d, J = 7.2 Hz, 2 H) 8.2 (s, 1 H) |
| 30 | 435.47 | | ES+ 436.4 | $^1$H NMR (300 MHz, chloroform-D) δ ppm 1.5 (s, 6 H) 2.5 (s, 3 H) 2.8 (m, 2 H) 3.1 (m, 2 H) 3.3 (t, J = 5.8 Hz, 2 H) 4.4 (t, J = 5.8 Hz, 2 H) 7.0 (s, 1 H) 7.3 (s, 1 H) 7.6 (m, 3 H) 8.1 (d, J = 7.2 Hz, 2 H) 8.4 (s, 1 H) |
| 31 | 408.49 | | ES− 407.5 | |
| 32 | 394.46 | | ES− 393.4 | |
| 33 | 312.32 | | ES− 311.4 | $^1$H NMR (300 MHz, chloroform-D) δ ppm 2.7 (m, 2 H) 3.1 (m, 2 H) 4.1 (s, 1 H) 4.7 (s, 2 H) 5.2 (s, 2 H) 7.0 (s, 1 H) 7.4 (m, 6 H) |

TABLE 2-continued

| Ex. No. | M | M.p. | LCMS | NMR |
|---|---|---|---|---|
| 34 | 407.42 | | ES+ 408.4 | $^1$H NMR (300 MHz, chloroform-D) δ ppm 2.5 (s, 3 H) 2.7 (m, 2 H) 3.1 (m, 2 H) 3.3 (t, J = 5.6 Hz, 2 H) 4.4 (t, J = 5.8 Hz, 2 H) 4.7 (s, 2 H) 5.0 (s, 1 H) 7.0 (s, 1 H) 7.2 (s, 1 H) 7.6 (m, 3 H) 8.1 (d, J = 7.4 Hz, 2 H) |
| 35 | 483.52 | | ES+ 484.5 | |
| 36 | 356.42 | 138-140 | ES− 355.4 | $^1$H NMR (300 MHz, chloroform-D) δ ppm 0.9 (t, J = 7.2 Hz, 3 H) 1.5 (m, 4 H) 1.9 (m, 2 H) 2.5 (s, 3 H) 4.1 (t, J = 6.7 Hz, 2 H) 5.2 (s, 2 H) 6.9 (m, 1 H) 7.5 (t, J = 7.7 Hz, 1 H) 7.6 (m, 2 H) 7.7 (d, J = 7.6 Hz, 1 H) 8.1 (d, J = 7.8 Hz, 1 H) 8.2 (s, 1 H) |
| 37 | 396.48 | 140-150 (pâteux) | ES− 395.4 | $^1$H NMR (300 MHz, chloroform-D) δ ppm 1.1 (m, 5 H) 1.6 (m, 8 H) 2.5 (s, 3 H) 4.1 (t, J = 6.7 Hz, 2 H) 5.2 (s, 2 H) 6.9 (m, 1 H) 7.5 (t, J = 7.7 Hz, 1 H) 7.6 (m, 2 H) 7.7 (d, J = 7.6 Hz, 1 H) 8.1 (d, J = 7.6 Hz, 1 H) 8.2 (s, 1 H) |
| 38 | 471.51 | 198-200 | ES+ 472.4 | |
| 39 | 384.49 | 180 | ES− 383.4 | $^1$H NMR (300 MHz, DMSO-D6) δ ppm 0.9 (t, J = 7.1 Hz, 3 H) 1.4 (m, 4 H) 1.7 (m, 2 H) 2.6 (m, 2 H) 3.0 (m, J = 7.3, 7.3 Hz, 4 H) 5.3 (s, 2 H) 7.2 (s, 1 H) 7.4 (s, 1 H) 7.5 (t, J = 7.6 Hz, 1 H) 7.7 (d, J = 7.6 Hz, 1 H) 7.9 (d, J = 7.6 Hz, 1 H) 8.1 (s, 1 H) 13.0 (s, 1 H) |
| 40 | 418.51 | 205 | ES− 417.4 | $^1$H NMR (300 MHz, DMSO-D6) δ ppm 2.3 (s, 3 H) 2.6 (d, J = 11.1 Hz, 2 H) 3.0 (s, 2 H) 4.3 (s, 2 H) 5.3 (s, 2 H) 7.2 (m, 3 H) 7.3 (d, J = 7.8 Hz, 2 H) 7.5 (m, 2 H) 7.7 (d, J = 7.8 Hz, 1 H) 7.9 (d, J = 7.8 Hz, 1 H) 8.0 (s, 1 H) 13.0 (s, 1 H) |
| 41 | 334.37 | 129-130 | ES+ 357.3 335.3 ES− 333.3 | $^1$H NMR (300 MHz, chloroform-D) δ ppm 5.2 (s, 2 H) 5.2 (s, 2 H) 6.9 (m, 4 H) 7.3 (m, 3 H) 7.5 (m, 3 H) 7.7 (d, J = 7.8 Hz, 1 H) 8.1 (d, J = 7.8 Hz, 1 H) 8.2 (s, 1 H) |
| 42 | 394.46 | | | $^1$H NMR (300 MHz, DMSO-D6) δ ppm 1.2 (m, 6 H) 1.7 (m, 5 H) 2.5 (m, 2 H) 3.0 (d, J = 5.0 Hz, 2 H) 3.9 (d, J = 5.9 Hz, 2 H) 5.2 (s, 2 H) 7.1 (s, 1 H) 7.2 (s, 1 H) 7.5 (t, J = 7.6 Hz, 1 H) 7.7 (d, J = 7.4 Hz, 1 H) 7.9 (d, J = 7.6 Hz, 1 H) 8.1 (s, 1 H) 13.0 (s, 1 H) |
| 43 | 448.54 | | ES− 447.4 | $^1$H NMR (300 MHz, DMSO-D6) δ ppm 2.6 (m, 2 H) 3.0 (m, 4 H) 3.2 (m, 2 H) 3.7 (s, 3 H) 5.3 (s, 2 H) 6.9 (m, 2 H) 7.2 (m, 3 H) 7.4 (s, 1 H) 7.5 (m, 1 H) 7.7 (m, 1 H) 7.9 (m, 1 H) 8.1 (s, 1 H) 13.0 (s, 1 H) |
| 44 | 436.50 | | ES− 435.3 | $^1$H NMR (300 MHz, DMSO-D6) δ ppm 7.4 (m, 2 H) 7.7 (dd, J = 15.5, 7.2 Hz, 4 H) 8.0 (m, 2 H) 10.1 (s, 2 H) 11.9 (m, 3 H) 12.1 (m, 2 H) 12.2 (s, 1 H) 12.3 (t, J = 7.6 Hz, 1 H) 12.4 (d, J = 7.6 Hz, 1 H) 12.7 (d, J = 7.6 Hz, 1 H) 12.8 (s, 1 H) 17.8 (s, 1 H) |
| 45 | 418.51 | | ES− 417.3 | $^1$H NMR (300 MHz, DMSO-D6) δ ppm 2.3 (s, 3 H) 2.6 (m, 2 H) 3.0 (m, 2 H) 4.3 (s, 2 H) 5.3 (s, 2 H) 7.2 (m, 5 H) 7.5 (m, 2 H) 7.7 (m, 1 H) 7.9 (m, 1 H) 8.0 (s, 1 H) 13.0 (s, 1 H) |
| 46 | 422.47 | | ES− 421.3 | $^1$H NMR (300 MHz, DMSO-D6) δ ppm 2.6 (dd, J = 6.5, 4.6 Hz, 2 H) 3.0 (m, 2 H) 4.3 (s, 2 H) 5.3 (s, 2 H) 7.2 (m, 3 H) 7.5 (m, 4 H) 7.7 (d, J = 7.8 Hz, 1 H) 7.9 (d, J = 7.8 Hz, 1 H) 8.1 (s, 1 H) 13.0 (s, 1 H) |
| 47 | 314.38 | 106-108 | ES+ 337.3 315.3 ES− 313.3 | $^1$H NMR (300 MHz, chloroform-D) δ ppm 0.9 (t, J = 7.2 Hz, 3 H) 1.4 (m, 4 H) 1.9 (m, 2 H) 4.0 (t, J = 6.7 Hz, 2 H) 5.2 (s, 2 H) 6.9 (m, 4 H) 7.5 (t, J = 7.7 Hz, 1 H) 7.7 (d, J = 8.2 Hz, 1 H) 8.1 (d, J = 7.8 Hz, 1 H) 8.2 (s, 1 H) |
| 48 | 422.47 | | ES− 421.3 | NMR $^1$H (300 MHz, DMSO-D6) δ ppm 2.6 (m, 2 H) 3.0 (m, 2 H) 4.4 (s, 2 H) 5.3 (s, 2 H) 7.1 (m, 1 H) 7.2 (s, 1 H) |

TABLE 2-continued

| Ex. No. | M | M.p. | LCMS | NMR |
|---|---|---|---|---|
| | | | | 7.4 (m, 3 H) 7.5 (m, 2 H) 7.7 (d, J = 7.8 Hz, 1 H) 7.9 (d, J = 7.8 Hz, 1 H) 8.1 (s, 1 H) 13.0 (s, 1 H) |
| 49 | 370.47 | | ES− 369.3 | $^1$H NMR (300 MHz, DMSO-D6) δ ppm 0.9 (t, J = 7.3 Hz, 3 H) 1.5 (m, 2 H) 1.6 (m, 2 H) 2.6 (dd, J = 6.5, 4.8 Hz, 2 H) 3.0 (m, 4 H) 5.3 (s, 2 H) 7.2 (s, 1 H) 7.4 (s, 1 H) 7.5 (t, J = 7.6 Hz, 1 H) 7.7 (d, J = 7.6 Hz, 1 H) 7.9 (d, J = 7.6 Hz, 1 H) 8.1 (s, 1 H) 13.0 (s, 1 H) |
| 50 | 429.47 | 136-138 | ES+ 430.4 ES− 428.4 | $^1$H NMR (300 MHz, chloroform-D) δ ppm 2.3 (s, 3 H) 3.1 (t, J = 6.6 Hz, 2 H) 4.3 (t, J = 6.6 Hz, 2 H) 5.1 (s, 2 H) 6.9 (m, 4 H) 7.4 (m, 4 H) 7.7 (d, J = 7.8 Hz, 1 H) 8.0 (m, 2 H) 8.1 (d, J = 7.8 Hz, 1 H) 8.2 (s, 1 H) |
| 51 | 354.44 | 127-129 | ES+ 377.4 355.4 ES− 353.4 | $^1$H NMR (300 MHz, chloroform-D) δ ppm 1.0 (m, 2 H) 1.2 (m, 3 H) 1.6 (m, 8 H) 4.1 (t, J = 6.8 Hz, 2 H) 5.2 (s, 2 H) 6.9 (m, 4 H) 7.5 (t, J = 7.7 Hz, 1 H) 7.8 (d, J = 8.0 Hz, 1 H) 8.1 (d, J = 7.8 Hz, 1 H) 8.2 (s, 1 H) |
| 52 | 300.31 | 199-200 | ES− 299.3 | $^1$H NMR (300 MHz, DMSO-D6) δ ppm 2.5 (s, 3 H) 3.9 (s, 3 H) 5.2 (s, 2 H) 7.1 (d, J = 8.6 Hz, 1 H) 7.5 (m, 2 H) 7.7 (m, 2 H) 7.9 (m, 1 H) 8.0 (s, 1 H) 13.0 (s, 1 H) |
| 53 | 328.36 | 169-170 | ES− 327.4 | $^1$H NMR (300 MHz, DMSO-D6) δ ppm 1.0 (t, J = 7.4 Hz, 3 H) 1.8 (m, 2 H) 2.5 (t, 3 H) 4.0 (t, J = 6.5 Hz, 2 H) 5.2 (s, 2 H) 7.1 (d, J = 8.6 Hz, 1 H) 7.5 (m, 2 H) 7.6 (dd, J = 8.4, 2.1 Hz, 1 H) 7.7 (d, J = 7.8 Hz, 1 H) 7.9 (d, J = 7.6 Hz, 1 H) 8.1 (s, 1 H) 13.0 (s, 1 H) |
| 54 | 344.41 | 95-96 | ES− 343.4 | $^1$H NMR (300 MHz, chloroform-D) δ ppm 0.9 (m, 3 H) 1.4 (m, 4 H) 1.8 (m, 2 H) 3.7 (s, 3 H) 4.0 (q, J = 6.9 Hz, 2 H) 5.2 (s, 2 H) 6.4 (dd, J = 8.8, 2.9 Hz, 1 H) 6.5 (m, 1 H) 6.9 (d, J = 8.8 Hz, 1 H) 7.5 (m, 1 H) 7.7 (d, J = 7.8 Hz, 1 H) 8.1 (d, J = 7.8 Hz, 1 H) 8.2 (s, 1 H) |
| 55 | 384.47 | 90-95 | ES− 383.4 | $^1$H NMR (300 MHz, chloroform-D) δ ppm 1.1 (m, 5 H) 1.6 (m, 8 H) 3.7 (s, 3 H) 4.0 (t, J = 6.9 Hz, 2 H) 5.2 (s, 2 H) 6.4 (dd, J = 8.8, 2.9 Hz, 1 H) 6.6 (m, J = 2.9 Hz, 1 H) 6.9 (d, J = 8.8 Hz, 1 H) 7.5 (m, 1 H) 7.7 (d, J = 7.6 Hz, 1 H) 8.1 (d, J = 7.8 Hz, 1 H) 8.2 (s, 1 H) |
| 56 | 385.46 | 160 | ES+ 386.3 ES− 384.3 | $^1$H NMR (300 MHz, DMSO-D6) δ ppm 0.9 (t, J = 7.1 Hz, 3 H) 1.1 (t, J = 7.2 Hz, 3 H) 1.4 (m, 4 H) 1.7 (m, 2 H) 3.3 (m, 2 H) 4.0 (t, J = 6.5 Hz, 2 H) 5.2 (s, 2 H) 7.0 (d, J = 8.6 Hz, 1 H) 7.5 (m, 3 H) 7.7 (d, J = 7.6 Hz, 1 H) 7.9 (m, 1 H) 8.1 (s, 1 H) 8.3 (t, J = 5.2 Hz, 1 H) 13.0 (s, 1 H) |
| 57 | 413.51 | | ES+ 414.3 Es− 412.4 | $^1$H NMR (300 MHz, DMSO-D6) δ ppm 0.9 (t, J = 6.9 Hz, 3 H) 1.0 (s élargi, 6 H) 1.4 (m, 4 H) 1.7 (m, 2 H) 3.3 (s élargi, 4 H) 4.0 (m, 2 H) 5.2 (s, 2 H) 7.0 (m, 3 H) 7.5 (t, J = 7.6 Hz, 1 H) 7.7 (d, J = 7.2 Hz, 1 H) 7.9 (d, J = 7.2 Hz, 1 H) 8.0 (s, 1 H) 13.0 (s, 1 H) |
| 58 | 425.52 | | ES+ 426.3 ES− 424.4 | $^1$H NMR (300 MHz, DMSO-D6) δ ppm 0.9 (t, J = 6.5 Hz, 3 H) 1.4 (m, 10 H) 1.7 (s, 2 H) 3.4 (s élargi, 4 H) 4.0 (m, 2 H) 5.2 (s, 2 H) 7.0 (m, 3 H) 7.5 (m, 1 H) 7.7 (m, 1 H) 7.9 (m, 1 H) 8.0 (s, 1 H) 13.0 (s élargi, 1 H) |
| 59 | 408.49 | | ES+ 409.3 ES− 407.3 | $^1$H NMR (300 MHz, DMSO-D6) δ ppm 1.0 (m, 8 H) 1.7 (m, 8 H) 4.1 (t, J = 6.6 Hz, 2 H) 5.2 (s, 2 H) 7.2 (s, 1 H) 7.2 (s, 1 H) 7.5 (t, J = 7.6 Hz, 1 H) 7.7 (d, J = 7.6 Hz, 1 H) 7.9 (d, J = 7.8 Hz, 1 H) 8.0 (s, 1 H) 13.0 (s, 1 H) |
| 60 | 371.43 | 178 | ES+ 372.3 ES− 370.4 | $^1$H NMR (300 MHz, DMSO-D6) δ ppm 0.9 (t, J = 7.0 Hz, 3 H) 1.4 (m, 4 H) 1.7 (m, 2 H) 2.8 (d, J = 4.2 Hz, 3 H) 4.0 (t, J = 6.4 Hz, 2 H) 5.2 (s, 2 H) 7.0 (d, J = 8.4 |

TABLE 2-continued

| Ex. No. | M | M.p. | LCMS | NMR |
|---|---|---|---|---|
| | | | | Hz, 1 H) 7.5 (m, 3 H) 7.7 (d, J = 7.4 Hz, 1 H) 7.9 (d, J = 7.4 Hz, 1 H) 8.1 (s, 1 H) 8.3 (d, J = 4.4 Hz, 1 H) 13.0 (s, 1 H) |
| 61 | 429.47 | 176-178 | ES+ 430.3 ES− 428.3 | $^1$H NMR (300 MHz, DMSO-D6) δ ppm 2.3 (s, 3 H) 2.9 (t, J = 6.3 Hz, 2 H) 4.2 (t, J = 6.4 Hz, 2 H) 5.1 (s, 2 H) 6.9 (m, 2 H) 7.0 (m, 2 H) 7.5 (m, 5 H) 7.9 (m, 4 H) 12.9 (8, 1 H) |
| 62 | 445.47 | | ES+ 446.1 ES− 444.3 | $^1$H NMR (300 MHz, chloroform-D) δ ppm 2.3 (s, 3 H) 3.7 (s, 3 H) 5.0 (s, 2 H) 5.2 (s, 2 H) 6.4 (dd, J = 8.7, 2.8 Hz, 1 H) 6.6 (d, J = 2.7 Hz, 1 H) 7.0 (d, J = 8.8 Hz, 1 H) 7.4 (m, 4 H) 7.7 (d, J = 7.6 Hz, 1 H) 8.0 (m, 3 H) 8.2 (s, 1 H) |
| 63 | 462.97 | | ES+ 427.3 ES− 425.4 | $^1$H NMR (300 MHz, chloroform-D) δ ppm 0.9 (t, J = 7.1 Hz, 3 H) 1.4 (m, 4 H) 1.9 (dd, J = 14.2, 6.6 Hz, 2 H) 3.2 (s, 4 H) 3.8 (m, 4 H) 4.1 (t, J = 6.6 Hz, 2 H) 5.3 (s, 2 H) 6.9 (m, 2 H) 7.1 (m, 1 H) 7.5 (t, J = 7.6 Hz, 1 H) 7.7 (d, J = 8.0 Hz, 1 H) 8.0 (d, J = 8.0 Hz, 1 H) 8.1 (s, 1 H) |
| 64 | 459.50 | 135-140 | ES+ 460.2 ES− 458.2 | $^1$H NMR (300 MHz, chloroform-D) δ ppm 2.3 (s, 3 H) 3.0 (t, J = 6.7 Hz, 2 H) 3.7 (s, 3 H) 4.3 (t, J = 6.7 Hz, 2 H) 5.1 (s, 2 H) 6.4 (m, 1 H) 6.5 (d, J = 2.9 Hz, 1 H) 6.9 (d, J = 8.8 Hz, 1 H) 7.4 (m, 4 H) 7.7 (d, J = 7.8 Hz, 1 H) 8.0 (m, 2 H) 8.0 (m, J = 7.8 Hz, 1 H) 8.2 (s, 1 H) |

Results

The measurement of the PPAR activation was performed according to a technique described by Lehmann et al. (*J. Biol. Chem.,* 270, (1995), 12953-12956).

CV-1 cells (monkey kidney cells) are cotransfected with an expression vector for the chimeric protein PPARγ-Gal4 and with a "reporter" plasmid that allows expression of the luciferase gene placed under the control of a promoter comprising Gal4 response elements.

The cells are seeded in 96-well microplates and cotransfected using a commercial reagent with the reporter plasmid (pG5-tk-pGL3) and the expression vector for the chimeric protein (PPARγ-Gal4). After incubation for 4 hours, whole culture medium (comprising 10% foetal calf serum) is added to the wells. After 24 hours, the medium is removed and replaced with whole medium comprising the test products. The products are left in contact with the cells for 18 hours. The cells are then lysed and the luciferase activity is measured using a luminometer. A PPARγ activation factor can then be calculated by means of the activation of the expression of the reporter gene induced by the product (relative to the control cells that have received no product).

In the absence of the PPARγ ligand binding domain (vector expressing Gal4 alone), the luciferase activity measured in the presence of an agonist is zero.

The following transactivation result was obtained with a concentration of 10 μM on PPARγ.

| Ex. | Concentration | Activation factor of the chimeric protein PPARγ-Gal4 |
|---|---|---|
| 7 | 10 μM | 9.10 |
| Without agonist (Control) | — | 1 |

Example of Biological Activities of Partial Agonists

Transactivation Test

The transactivation test using the expression of a chimeric protein Gal-4-PPARγ makes it possible to determine also whether an agonist functions as a "full" agonist or as a "partial" agonist in this system.

An agonist is "partial" in this system if it induces a weaker response, i.e. it has lower efficacy, than rosiglitazone, which is a "full" agonist. In concrete terms, in our system, the transactivation obtained at the plateau with a partial agonist will be between 20% and 50% of the maximum response (efficacy) at the plateau of rosiglitazone.

| Ex. | Maximum stimulation of the PPARγ chimeric protein obtained with rosiglitazone | Concentration to reach the maximum stimulation of the PPARγ chimeric protein |
|---|---|---|
| 4 | 28% | 12.5 μM |

The invention claimed is:

1. A compound of formula (1) :

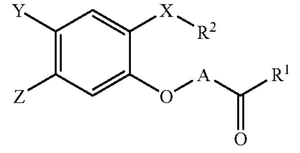

(6)

in which:

$R^1$ represents —O—$R'^1$ or —$NR'^1R''^1$, with $R'^1$ and $R''^1$, which may be identical or different, being a hydrogen atom, an alkyl radical, an alkenyl radical, an alkynyl radical, a cycloalkyl radical, an aryl radical or a heteroaryl radical;

A represents a linear or branched, saturated or unsaturated divalent hydrocarbon-based radical containing from 1 to 10 carbon atoms;

$R^2$ is:

propyl, isopropyl, butyl, isobutyl, tert-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl, 7,7-dimethyloctyL alkenyl or alkynyl;

an optionally substituted cycloalkylalkyl radical; or an optionally substituted heterocyclylalkyl radical;

X is chosen from an oxygen atom and a sulfur atom;

Y and Z, which may be identical or different, are independently of each other, a hydrogen atom, a halogen atom, an alkyl radical and a radical —O—$R^3$, —C(O)—$R^3$, —C(O)—$NHR^3$ or —C(O)—$NR^3R^4$; or Y and Z together form, with the carbon atoms that bear them, a 5-membered ring comprising a ketone function; and $R^3$ and $R^4$, which may be identical or different, are independently of each other, a hydrogen atom and an alkyl radical, or $R^3$ and $R^4$ together form, with the nitrogen atom that bears them, an optionally substituted heterocycle;

or optical isomersor oxides thereof, or pharmaceutically acceptable addition salts thereof with acids or bases.

2. The compound according to claim 1, having one or more of the following characteristics, taken separately or as a combination of one, several or all of them:

$R^1$ represents —O—$R'^1$, with $R'^1$ being a hydrogen atom or an alkyl radical;

A represents a linear or branched, saturated or unsaturated divalent hydrocarbon-based radical containing from 1 to 6 carbon atoms, or a linear or branched hydrocarbon-based chain containing from 1 to 6 carbon atoms, linked to an ortho-, meta- or para-phenylene ring;

$R^2$ is propyl, isopropyl, butyl, isobutyl, tert-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl, 7,7-dimethyloctyl, a cycloalkylalkyl radical, or a heterocyclylalkyl radical, which is optionally substituted;

X is an oxygen atom or a sulfur atom;

Y and Z, which may be identical or different, are independently of each other, a hydrogen atom, a halogen atom and a radical —O—$R^3$, —C(O)—$R^3$, —C(O)—$NHR^3$ or —C(O)—$NR^3R^4$; or Y and Z together form, with the carbon atoms that bear them, a 5-membered ring comprising a ketone function; and $R^3$ and $R^4$, which may be identical or different, are independently of each other, a hydrogen atom or an alkyl radical containing from 1 to 4 carbon atoms, or $R^3$ and $R^4$ together form, with the nitrogen atom that bears them, a 6-membered heterocycle optionally comprising another hetero atom (other than the nitrogen atom that bears them), which is N, O and S;

or optical isomersor oxides thereof, or pharmaceutically acceptable addition salts thereof with acids or bases.

3. The compound according to claim 1, having one or more of the following characteristics, taken separately or as a combination of one, several or all of them:

$R^1$ represents —O—$R'^1$, with $R'^1$ being a hydrogen atom, a methyl radical or an ethyl radical;

A represents a linear or branched, saturated or unsaturated divalent hydrocarbon-based radical containing from 1 to 3 carbon atoms, or a linear or branched hydrocarbon-based chain containing from 1 to 3 carbon atoms, linked to an ortho- , meta- or para-phenylene ring;

$R^2$ is propyl, isopropyl, butyl, isobutyl, tert-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl, 7,7-dimethyloctyl, a cycloalkylalkyl radical, or a heterocyclylalkyl radical, which is optionally substituted;

X is an oxygen atom or a sulfur atom;

Y and Z, which may be identical or different, are independently of each other, a hydrogen atom, a halogen atom and a radical —O—$R^3$, —C(O)—$R^3$, —C(O)—$NHR^3$ or —C(O)—$NR^3R^4$; or Y and Z together form, with the carbon atoms that bear them, a 5-membered ring comprising a ketone function; and $R^3$ and $R^4$, which may be identical or different, are independently of each other, a hydrogen atom or an alkyl radical containing from 1 to 3 carbon atoms, or $R^3$ and $R^4$ together form, with the nitrogen atom that bears them, a 6-membered heterocycle optionally comprising another hetero atom (other than the nitrogen atom that bears them), which is N, O and S;

or optical isomersor oxides thereof, or pharmaceutically acceptable addition salts thereof with acids or bases.

4. The compound according to claim 1, having one or more of the following characteristics, taken separately or as a combination of one, several or all of them:

$R^1$ represents a hydroxyl radical;

A represents —$CH_2$—, —$(CH_2)_3$—, —$C(CH_3)_2$—, —$CH_2$-m-phenylene or —$CH_2$-o-phenylene;

$R^2$ is propyl, isopropyl, butyl, isobutyl, tert-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl, 7,7-dimethyloctyl, a cycloalkylalkyl radical, or a heterocyclylalkyl radical, which is optionally substituted;

X is an oxygen atom or a sulfur atom;

Y and Z, which may be identical or different, are independently of each other, a hydrogen atom, a halogen atom or a radical —O—$R^3$, —C(O)—$R^3$, —C(O)—$NHR^3$ or —C(O)—$NR^3R^4$; or Y and Z together form, with the carbon atoms that bear them, a 5-membered ring comprising a ketone function; and $R^3$ and $R^4$, which may be identical or different, are independently of each other, a hydrogen atom, a methyl radical and an ethyl radical, or $R^3$ and $R^4$ together form, with the nitrogen atom that bears them, a saturated 6-membered heterocycle optionally comprising another hetero atom (other than the nitrogen atom that bears them), chosen from N and O;

or optical isomersor oxides thereof, or pharmaceutically acceptable addition salts thereof with acids or bases.

5. The compound according to claim 1, wherein the substituents of the radicals of the compounds of the formula (1) are halogen atoms, methyl, ethyl, methoxy, phenyl, trifluoromethyl or trifluoromethoxy radicals.

6. The compound according to claim 1, wherein the heterocyclic radicals are thienyl, benzothiophenyl, pyridyl, morpholino, piperidino or oxazolyl radicals.

7. A compound which is:

4-[6-(2-cyclohexylethoxy)-3-oxoindan-5-yloxy]butanoic acid;

4-(6-hexyloxy-3-oxoindan-5-yloxy)butanoic acid;

4-(3-oxo-6-pentyloxyindan-5-yloxy)butanoic acid;

3-(3-oxo-6-propylsulfanylindan-5-yloxymethyl)benzoic acid;

4-(6-cyclohexylmethoxy-3-oxoindan-5-yloxy)butanoic acid;

3-(3-oxo-6-pentyloxyindan-5-yloxymethyl)benzoic acid;

4-(3-oxo-6-pentyloxyindan-5-yloxymethyl)benzoic acid;

3-[6-(3-methylbenzylsulfanyl)-3-oxoindan-5-yloxymethyl]benzoic acid;

4-[6-(5-methyl-2-phenyloxazol-4-ylmethoxy)-3-oxoindan-5-yloxy]butanoic acid;

3-[6-(4-fluorobenzylsulfanyl)-3-oxoindan-5-yloxymethyl]benzoic acid;

3-[6-(3-fluorobenzylsulfanyl)-3-oxoindan-5-yloxymethyl]benzoic acid;

3-[6-(4-methylbenzylsulfanyl)-3-oxoindan-5-yloxymethyl]benzoic acid;

3-{6-[2-(4-methoxyphenyl)ethylsulfanyl]-3-oxoindan-5-yloxymethyl}benzoic acid;

3-(6-cyclohexylmethoxy-3-oxoindan-5-yloxymethyl)benzoic acid;

2-methyl-2-(3-oxo-6-pentyloxyindan-5-yloxy)propanoic acid;

2-methyl-2-(3-oxo-6-phenethyloxyindan-5-yloxy)propanoic acid;

3-(3-oxo-6-phenethyloxyindan-5-yloxymethyl)benzoic acid;

3-{2-[2-(5-methyl-2-phenyloxazol-4-yl)ethoxy]phenoxymethyl}benzoic acid;

3-[2-(2-cyclohexylethoxy)phenoxymethyl]benzoic acid;

3-(5-methoxy-2-pentyloxyphenoxymethyl)benzoic acid; and 3-(5-diethylcarbamoyl-2-pentyloxyphenoxymethyl)benzoic acid;

or optical isomersor oxides thereof, or pharmaceutically acceptable addition salts with acids or bases.

8. A process for the preparation of a compound according to claim 1, comprising reacting the —X—H moiety of a compound of formula (2):

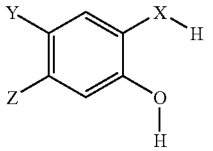

(2)

in which X, Y and Z are as defined in claim 1, with a compound of the formula (3):

Hal-$R^2$ (3)

in which Hal represents a halogen atom, in the presence of a base, optionally in the presence of an activator, in polar aprotic medium, to give a compound of formula (4):

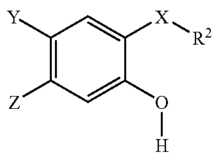

(4)

in which $R^2$, X, Y and Z are as defined in claim 1, reacting a compound of the formula (4) under similar conditions, with a halide of formula (5):

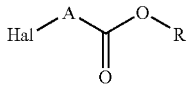

(5)

in which Hal represents a halogen atom and R represents an acid function protecting group, to give a compound of formula (6)

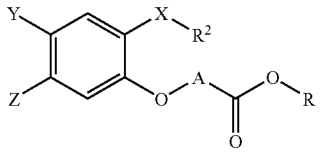

(6)

in which R, $R^2$, X, Y and Z are as defined in claim 1, removing protecting group R to give an acid of formula ($1_{OH}$):

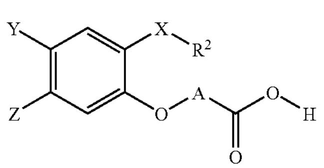

($1_{OH}$)

which is a special case of the compounds of the formula (1) in which $R^1$ represents a hydroxyl radical, and optionally esterifying ($1_{OH}$), or converting into a corresponding amide, to give compounds of formula (1) with $R^1$ other than a hydroxyl radical.

9. A pharmaceutical composition comprising a pharmaceutically effective amount of at least one compound of formula (1) obtained via the process according to claim 8, in combination with one or more pharmaceutically acceptable vehicles.

10. A method of treating dyslipidaemia, atherosclerosis or diabetes comprising administering a compound of claim 1.

11. A pharmaceutical composition comprising a pharmaceutically effective amount of at least one compound of formula (I) according to claim 1, in combination with one or more pharmaceutically acceptable vehicles.

12. A compound of formula (1'):

(1')

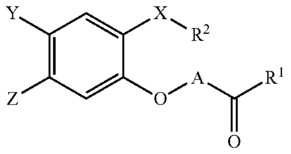

in which:

$R^1$ represents —O—$R'^1$ or —$NR'^1R''^1$, with $R'^1$ and $R''^1$, which may be identical or different, being a hydrogen atom, an alkyl radical, an alkenyl radical, an alkynyl radical, a cycloalkyl radical, an aryl radical or a heteroaryl radical;

A represents a linear or branched, saturated or unsaturated divalent hydrocarbon-based radical containing from 1 to 10 carbon atoms;

$R^2$ is:

an alkyl, alkenyl or alkynyl radical;

an optionally substituted cycloalkylalkyl radical;

an optionally substituted arylalkyl radical; or an optionally substituted heterocyclylalkyl radical;

X is chosen from an oxygen atom and a sulfur atom;

Y is a hydrogen atom, a halogen atom, an alkyl radical and a radical —O—$R^3$, —C(O)—$R^3$, —C(O)—$NHR^3$ or —C(O)—$NR^3R^4$;

Z is —C(O)$NR^3R^4$ and $R^3$ and $R^4$ together form, with the nitrogen atom that bears them, a piperazine ring, or optical isomersor oxides thereof, or pharmaceutically acceptable addition salts thereof with acids or bases.

13. A compound of formula (1):

(1)

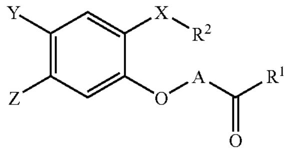

in which:

$R^1$ represents —O—$R'^1$ or —$NR'^1R''^1$, with $R'^1$ and $R''^1$, which may be identical or different, being a hydrogen atom, an alkyl radical, an alkenyl radical, an alkynyl radical, a cycloalkyl radical, an aryl radical or a heteroaryl radical;

A represents a linear or branched, saturated or unsaturated divalent hydrocarbon-based radical containing from 1 to 10 carbon atoms;

$R^2$ is:

an alkyl, alkenyl or alkynyl radical;

an optionally substituted cycloalkylalkyl radical;

an optionally substituted arylalkyl radical; or an optionally substituted heterocyclylalkyl radical;

X is chosen from an oxygen atom and a sulfur atom;

Y is a hydrogen atom, a halogen atom, an alkyl radical and a radical —O—$R^3$, —C(O)—$R^3$, —C(O)—$NHR^3$ or —C(O)—$NR^3R^4$;

Z is —C(O)$NR^3R^4$ and $R^3$ and $R^4$ together form, with the nitrogen atom that bears them, piperidine ring, or optical isomersor oxides thereof, or pharmaceutically acceptable addition salts thereof with acids or bases.

* * * * *

UNITED STATES PATENT AND TRADEMARK OFFICE

CERTIFICATE OF CORRECTION

PATENT NO. : 8,653,134 B2
APPLICATION NO. : 11/813933
DATED : February 18, 2014
INVENTOR(S) : Vidal et al.

It is certified that error appears in the above-identified patent and that said Letters Patent is hereby corrected as shown below:

On the Title Page, Item (54) and in the Specification, Column 1, Lines 1-5, Title reads "HYDROXYPHENOL DERIVATIVES, PROCESSES FOR THE PREPARATION THEREOF, PHARMACEUTICAL COMPOSITIONS THEM, AND THERAPEUTIC USES THEREOF" should read -- HYDROXYPHENOL DERIVATIVES, PROCESSES FOR THE PREPARATION THEREOF, PHARMACEUTICAL COMPOSITIONS COMPRISING THEM, AND THERAPEUTIC USES THEREOF --

In the Specification

Column 43, line 12 reads "thylnonyl, 3,7-dimethyloctyl, 7,7-dimethyloctyL alk-" should read -- thylnonyl, 3,7-dimethyloctyl, 7,7-dimethyloctyl, alk- --

Signed and Sealed this
Twenty-ninth Day of July, 2014

Michelle K. Lee
*Deputy Director of the United States Patent and Trademark Office*

UNITED STATES PATENT AND TRADEMARK OFFICE

CERTIFICATE OF CORRECTION

PATENT NO. : 8,653,134 B2
APPLICATION NO. : 11/813933
DATED : February 18, 2014
INVENTOR(S) : Vidal et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 974 days.

Signed and Sealed this
Twenty-ninth Day of September, 2015

Michelle K. Lee
*Director of the United States Patent and Trademark Office*